(12) United States Patent
Betz et al.

(10) Patent No.: US 11,723,778 B1
(45) Date of Patent: Aug. 15, 2023

(54) VERTEBRAL IMPLANT SYSTEM AND METHODS OF USE

(71) Applicant: NOFUSCO Corporation, Bradenton, FL (US)

(72) Inventors: Randal R. Betz, Ocean City, NJ (US); Dale E. Whipple, Nashua, NH (US)

(73) Assignee: NOFUSCO CORPORATION, Bradenton, FL (US)

( * ) Notice: Subject to any disclaimer, the term of this patent is extended or adjusted under 35 U.S.C. 154(b) by 0 days.

(21) Appl. No.: 17/934,874

(22) Filed: Sep. 23, 2022

Related U.S. Application Data

(60) Provisional application No. 63/247,345, filed on Sep. 23, 2021.

(51) Int. Cl.
*A61F 2/44* (2006.01)
*A61B 17/064* (2006.01)
(Continued)

(52) U.S. Cl.
CPC ............ *A61F 2/44* (2013.01); *A61B 17/0642* (2013.01); *A61B 17/7059* (2013.01);
(Continued)

(58) Field of Classification Search
CPC ........... A61B 2017/00407; A61B 2017/00411; A61B 2017/00867; A61B 17/0642;
(Continued)

(56) References Cited

U.S. PATENT DOCUMENTS 583,455 A * 6/1897 Bush ............... A61B 17/8004
606/212
4,047,524 A 9/1977 Hall
(Continued)

FOREIGN PATENT DOCUMENTS

| AU | 2007317886 B2 | 3/2014 |
| EP | 2725994 B1 | 5/2017 |

(Continued)

OTHER PUBLICATIONS

Ahn, J., Tabaraee, E., Bohl, D.D., Singh, K., Surgical management of adult spinal deformity: Indications, surgical outcomes, and health-related quality of life. Seminars in Spine Surgery, 29(2), 72-76, 2017, 5 pgs., https://doi.org/10.1053/j.semss.2016.12.001, Chicago, IL, USA.

(Continued)

*Primary Examiner* — Larry E Waggle, Jr.
(74) *Attorney, Agent, or Firm* — John Brooks Law LLC; John H. Brooks, III

(57) ABSTRACT

A vertebral implant system is provided comprising a staple and a vertical member. In some embodiments, the vertical member is an adjustable member. In some embodiments, the adjustable member is configured to be adjusted by a small diameter tool or an electromagnetic mechanism. In some embodiments, the adjustable member is a strain inducer adjusted by a radio frequency receiver and transmitter. In some embodiments, the vertical member is a plate or a bracket. In some embodiments, the vertebral implant system is configured to be installed from an anterior, oblique, or lateral angle to the vertebral body. In some embodiments, a self adjusting screw plate alignment system is provided comprising a bone screw having threaded and tip portions, (Continued)

a plate with a through hole, a locking element and a securing element configured to frictionally anchor the tip portion of the bone screw in the plate through hole.

16 Claims, 24 Drawing Sheets

(51) Int. Cl.
  *A61B 17/70* (2006.01)
  *A61B 17/80* (2006.01)
  *A61B 17/00* (2006.01)
(52) U.S. Cl.
  CPC ...... *A61B 17/8009* (2013.01); *A61B 17/8014* (2013.01); *A61B 17/8019* (2013.01); *A61B 17/8052* (2013.01); *A61B 2017/00407* (2013.01); *A61B 2017/00411* (2013.01); *A61B 2017/00867* (2013.01)
(58) Field of Classification Search
  CPC ..... A61B 17/70; A61B 17/7059; A61B 17/80; A61B 17/8004; A61B 17/8009; A61B 17/8023; A61B 17/8061; A61B 17/809; A61F 2/44
  See application file for complete search history.

(56) References Cited

U.S. PATENT DOCUMENTS

| | | | |
|---|---|---|---|
| 4,289,123 | A | 9/1981 | Dunn |
| 4,615,338 | A * | 10/1986 | Ilizarov ............... A61B 17/62 606/58 |
| 4,657,550 | A * | 4/1987 | Daher ................. A61F 2/44 623/17.11 |
| 4,723,540 | A * | 2/1988 | Gilmer, Jr. ......... A61B 17/0642 411/456 |
| 5,395,372 | A | 3/1995 | Holt |
| 5,522,899 | A | 6/1996 | Michelson |
| 5,620,443 | A | 4/1997 | Gertzbein |
| 5,713,899 | A | 2/1998 | Mamay |
| 5,728,127 | A | 3/1998 | Asher |
| 5,947,969 | A | 9/1999 | Errico et al. |
| 5,951,553 | A | 9/1999 | Betz |
| 5,980,522 | A | 11/1999 | Koros et al. |
| 6,287,308 | B1 | 9/2001 | Betz |
| 6,527,803 | B1 | 3/2003 | Crozet et al. |
| 6,623,484 | B2 | 11/2003 | Betz |
| 6,821,298 | B1 | 11/2004 | Jackson |
| 6,984,234 | B2 | 1/2006 | Bray |
| 7,250,060 | B2 | 7/2007 | Trieu |
| 7,621,938 | B2 | 11/2009 | Molz, IV |
| 7,704,279 | B2 | 4/2010 | Moskowitz |
| 7,799,060 | B2 * | 9/2010 | Lange ............... A61B 17/7022 606/257 |
| 7,833,245 | B2 | 11/2010 | Kaes |
| 7,955,392 | B2 | 6/2011 | Dewey |
| 8,062,375 | B2 | 11/2011 | Glerum |
| 8,075,593 | B2 | 12/2011 | Hess |
| 8,097,037 | B2 | 1/2012 | Serhan |
| 8,157,842 | B2 | 4/2012 | Phan |
| 8,267,997 | B2 | 9/2012 | Colleran |
| 8,273,129 | B2 | 9/2012 | Baynham |
| 8,292,963 | B2 * | 10/2012 | Miller ............... A61F 2/44 606/252 |
| 8,353,913 | B2 | 1/2013 | Moskowitz |
| 8,409,287 | B2 | 4/2013 | Braddock, Jr |
| 8,454,623 | B2 | 6/2013 | Patel |
| 8,496,689 | B2 | 7/2013 | Massoudi |
| 8,545,567 | B1 | 10/2013 | Krueger |
| 8,603,142 | B2 | 12/2013 | Robinson |
| 8,721,686 | B2 | 5/2014 | Gordon |
| 8,845,731 | B2 | 9/2014 | Weiman |
| 8,845,732 | B2 | 9/2014 | Weiman |
| 8,870,961 | B2 | 10/2014 | Thalgott |
| 8,894,708 | B2 | 11/2014 | Thalgott |
| 8,945,184 | B2 | 2/2015 | Hess |
| 8,979,927 | B2 | 3/2015 | Huntsman |
| 9,050,143 | B2 | 6/2015 | May |
| 9,055,981 | B2 | 6/2015 | Lamborne |
| 9,107,760 | B2 | 8/2015 | Walters |
| 9,179,944 | B2 | 11/2015 | Boyer, II |
| 9,198,774 | B2 | 12/2015 | Pisharodi |
| 9,204,899 | B2 | 12/2015 | Buttermann |
| 9,283,091 | B2 | 3/2016 | Melkent |
| 9,375,238 | B2 | 6/2016 | Binder |
| 9,393,053 | B2 | 7/2016 | Fessler |
| 9,402,739 | B2 | 8/2016 | Weiman |
| 9,463,091 | B2 | 10/2016 | Brett |
| 9,566,166 | B2 | 2/2017 | Parry |
| 9,713,537 | B2 | 7/2017 | Bray, Jr. |
| 9,724,206 | B2 | 8/2017 | Aeschlimann |
| 9,750,618 | B1 | 9/2017 | Daffinson et al. |
| 9,763,805 | B2 | 9/2017 | Cheng |
| 9,795,485 | B2 | 10/2017 | Allain |
| 9,833,262 | B2 * | 12/2017 | Lim ................. A61B 17/7011 |
| 9,889,020 | B2 | 2/2018 | Baynham |
| 9,889,022 | B2 | 2/2018 | Moskowitz |
| 9,956,007 | B2 | 5/2018 | Choi |
| 9,956,087 | B2 | 5/2018 | Seifert |
| 9,987,144 | B2 | 6/2018 | Seifert |
| 10,028,740 | B2 | 7/2018 | Moskowitz |
| 10,137,001 | B2 | 11/2018 | Weiman |
| 10,143,501 | B2 | 12/2018 | Northcutt |
| 10,149,703 | B2 | 12/2018 | Moskowitz |
| 10,195,045 | B2 | 2/2019 | Muller |
| 10,231,756 | B2 | 3/2019 | Buss |
| 10,251,643 | B2 | 4/2019 | Moskowitz |
| 10,307,265 | B2 | 6/2019 | Sack |
| 10,307,268 | B2 | 6/2019 | Moskowitz |
| 10,405,992 | B2 | 9/2019 | Sack |
| 10,413,426 | B2 | 9/2019 | Parry |
| 10,448,979 | B2 | 10/2019 | Fox |
| 10,478,319 | B2 | 11/2019 | Moskowitz |
| 10,492,919 | B2 | 12/2019 | Rashbaum |
| 10,531,961 | B2 | 1/2020 | Dinville |
| 10,588,753 | B2 | 3/2020 | Whipple et al. |
| 10,603,084 | B1 | 3/2020 | Sanders |
| 10,660,673 | B2 | 5/2020 | Maly |
| 10,687,877 | B2 | 6/2020 | Lavigne |
| 10,702,391 | B2 | 7/2020 | Ameil |
| 10,779,816 | B2 | 9/2020 | Goldstein |
| 10,864,081 | B2 | 12/2020 | Tyber |
| 10,925,752 | B2 | 2/2021 | Weiman |
| 10,973,649 | B2 | 4/2021 | Weiman |
| 11,065,128 | B2 | 7/2021 | Zappacosta |
| 11,135,069 | B2 | 10/2021 | Eisen |
| 11,259,936 | B2 | 3/2022 | Betz |
| 11,484,415 | B2 | 11/2022 | Kim |
| 2005/0165485 | A1 | 7/2005 | Trieu |
| 2006/0095136 | A1 | 5/2006 | McLuen |
| 2010/0131010 | A1 * | 5/2010 | Graf ................. A61B 17/7007 606/264 |
| 2011/0125269 | A1 | 5/2011 | Moskowitz |
| 2013/0274810 | A1 | 10/2013 | Fraser et al. |
| 2014/0100662 | A1 | 4/2014 | Patterson et al. |
| 2014/0277154 | A1 | 9/2014 | Perry |
| 2015/0088256 | A1 | 3/2015 | Ballard |
| 2015/0105834 | A1 * | 4/2015 | Bilger ................. A61B 17/68 606/86 R |
| 2016/0106549 | A1 | 4/2016 | Vestgaarden |
| 2018/0028327 | A1 | 2/2018 | Ballard |
| 2019/0298421 | A1 * | 10/2019 | Capote ................. A61F 2/442 |
| 2021/0386556 | A1 | 12/2021 | Betz |
| 2022/0015751 | A1 * | 1/2022 | Chevalier .......... A61B 17/8009 |
| 2022/0387182 | A1 | 12/2022 | Bernard |

FOREIGN PATENT DOCUMENTS

| | | | |
|---|---|---|---|
| WO | 2004089256 | A1 | 10/2004 |
| WO | 2005007040 | A1 | 1/2005 |
| WO | 2005007041 | A1 | 1/2005 |
| WO | 2006086895 | A1 | 8/2006 |

(56) References Cited

FOREIGN PATENT DOCUMENTS

| WO | 2011057181 | A1 | 5/2011 |
|----|------------|-----|--------|
| WO | 2011057185 | A1 | 5/2011 |
| WO | 2014145478 | A1 | 9/2014 |
| WO | 2021230871 |     | 12/2021 |
| WO | 2021257484 |     | 12/2021 |

OTHER PUBLICATIONS

Magerl, F., Aebi, M., Gertzbein, S.D., Harms, J. Nazarian, S., A comprehensive classification of thoracic and lumbar injuries. European Spine Journal, 3(4), 184-201, 1994, 18 pgs., https://doi.org/10.1007/BF02221591.

Yang, Andres, Non-FInal Office Action for co-pending U.S. Appl. No. 15/402,112, dated Aug. 29, 2018, 9 pgs., USPTO, Alexandria VA, USA.

James Guille, The Feasibility, Safety, and Utility of Vertebral Wedge Osteotomies for the Fusionless Treatment of Paralytic Scoliosis SPINE vol. 28 No. 20s pp. S266-S274, 9 pgs., 2003, Lippincott Williams & Wlkins, Inc, USA.

Kevin McCarthy, Clinical Efficacy of the Vertebral Wedge Osteotomy for the Fusionless Treatment of Paralytic Scoliosis SPINE vol. 35 Number 4 pp. 403-410, 8 pgs., 2010 Lippincott, Williams & Wilkins, Inc., USA.

Betz RR; Cunningham B; Selgrath C; Drwery T; Sherman MC: Preclinical testing of a wedge-rod system for fusionless correction of scoliosis. Spine (Phila Pa 1976) 28(20S):S275-S278, 2003, 4 pgs., Philadelphia PA, USA.

Betz RR; Mulcahey MJ: New surgical treatments for scoliosis: vertebral body stapling and wedge osteotomies. Viewpoint, Shriners Hospitals for Children, www.shrinershq.org, Sep. 2001, as downloaded from www.SpineUniverse.com on Oct. 15, 2018, 4 pgs., USA.

Didelot, William P.; Kling, Thomas F. Jr.; Lindseth, Richard E.: Anterior Vertebral Osteotomies to Correct Lumbar Scoliosis Without Fusion, Ch. 47. In: Modern Anterior Scoliosis Surgery (Lenke, L.; Betz, R.; Harms, J., eds.), Thieme Medical Publishers, 2004, pp. 693-706, 7 pgs. (2 pgs per sheet), New York, USA.

Rodriquez, Kari, Written Opinion of the International Searching Authority for co-pending PCT Application No. PCT/US21/37285, dated Aug. 24, 2021, 7 pgs., United States Patent and Trademark Office, Alexandria, VA, USA.

Rodriquez, Kari, International Search Report for co-pending PCT Application No. PCT/US21/37285, dated Aug. 24, 2021, 2 pgs., United States Patent and Trademark Office, Alexandria, VA, USA.

Kamikawa, Tracy L., Office Action for parent U.S. Appl. No. 17/347,492, dated Aug. 6, 2021, 9 pgs., United States Patent and Trademark Office, Alexandria, VA, USA.

Kamikawa, Tracy L. Notice of Allowance for parent U.S. Appl. No. 17/347,492, dated Oct. 18, 2021, 21 pgs., United States Patent and Trademark Office, Alexandria, VA, USA.

Berven, Sigurd H.; Hu, Serena S.; Deviren, Vedat; Smith, Jason; Bradford, David S.: Lumbar End Plate Osteotomy in Adult Patients With Scoliosis, Jun. 2003, Clinical Orthopaedics and Related Research, No. 411, pp. 70-76, 7 pgs., San Francisco, CA, USA.

Kamikawa, Tracy L., Restriction Requirement for U.S. Appl. No. 17/676,609, dated May 13, 2022, 8 pgs., United States Patent and Trademark Office, Alexandria, VA, USA.

Kamikawa, Tracy L., Notice of Allowance for U.S. Appl. No. 17/676,609, dated Jun. 23, 2022, 24 pgs. United States Patent and Trademark Office, Alexandria, VA, USA.

Negrelli Rodriguez, Christina, Non-FInal Office Action for U.S. Appl. No. 15/404,129, dated Nov. 5, 2018, 26 pgs., USPTO, Alexandria VA, USA.

Negrelli-Rodriguez, Christina, Final Office Action for U.S. Appl. No. 15/404,129, dated Feb. 15, 2019, 20 pgs., USPTO, Alexandria VA, USA.

Negrelli-Rodriguez, Christina, Non-FInal Office Action for U.S. Appl. No. 15/404,129, dated Aug. 16, 2019, 8 pgs., USPTO, Alexandria VA, USA.

Negrelli-Rodriguez, Christina, Notice of Allowance for U.S. Appl. No. 15/404,129, dated Nov. 13, 2019, 5 pgs., USPTO, Alexandria VA, USA.

N.H. Hart, S. Nimphius, T. Rantalainen, A. Ireland, A. Siafaikass, R.U. Newton, Mechanical basis of bone strength: influence of bone material, bone structure and muscle action, Journal of Muscoloskeletal and Neuro Interacrtions, 26 pages, 17(3): 114-139, Sep. 2017, GR.

Kamikawa, Tracy L., Notice of Allowance for U.S. Appl. No. 17/676,609, dated Nov. 15, 2022, 5 pgs., United States Patent and Trademark Office, Alexandria, VA, USA.

Kamikawa, Tracy L., Notice of Allowance for U.S. Appl. No. 18/051,732, dated Feb. 2, 2023, 21 pgs., United States Patent and Trademark Office, Alexandria, VA, USA.

* cited by examiner

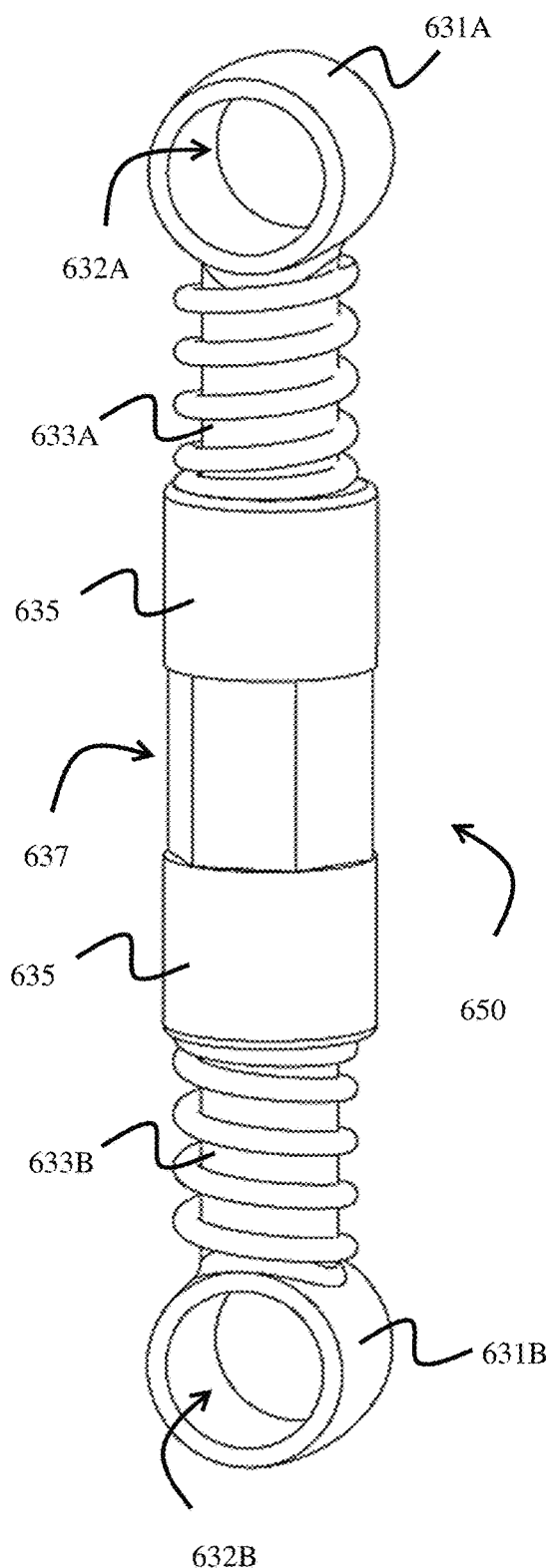
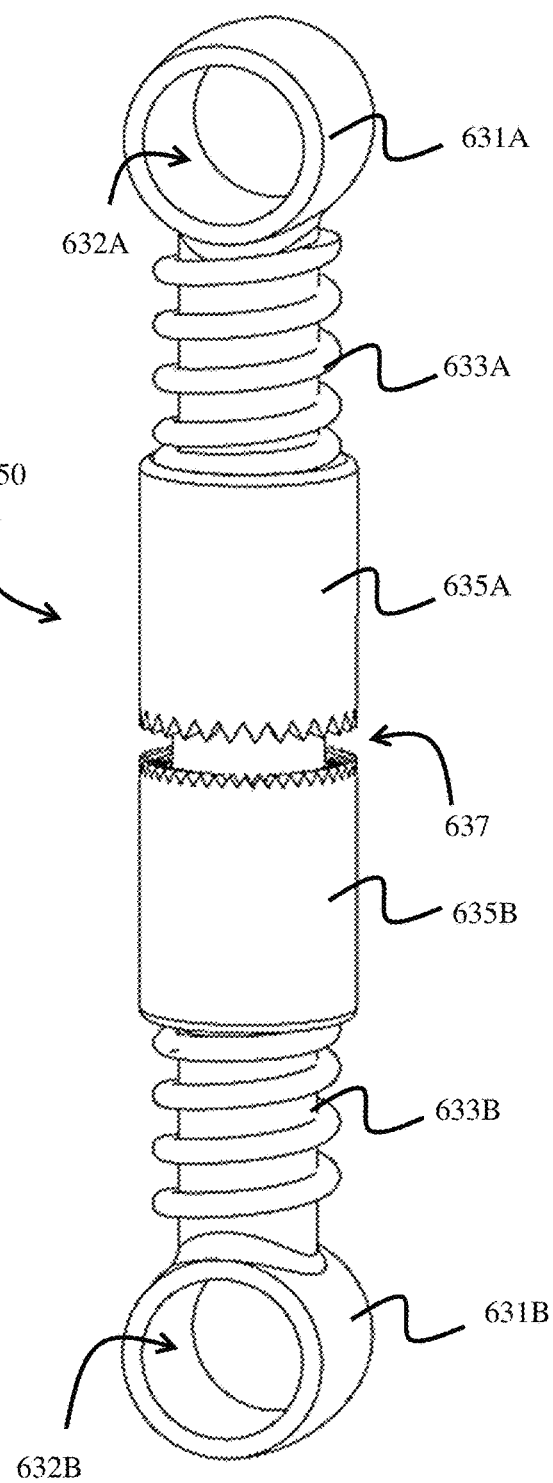
FIG. 6B          FIG. 6C

VERTEBRAL IMPLANT SYSTEM AND METHODS OF USE

CROSS-REFERENCE TO RELATED APPLICATIONS

This application claims benefit to U.S. Pat. App. No. 63/247,345, entitled "INTRAVERTEBRAL IMPLANT AND METHODS OF USE" filed on Sep. 23, 2021; the entire contents of which are incorporated herein by reference.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not applicable.

BACKGROUND OF THE INVENTION

1. Field of the Invention

This invention relates to spinal implants, in particular a vertebral implant system configured to alter the alignment of the spine. In some embodiments, the vertebral implant system comprises elements that may be adjusted after implantation.

2. Background

In the field of spinal correction, available literature supports that trauma and degenerative spinal conditions resulting in back pain and leg pain lead to debilitation, loss of work and life happiness.

Compression fractures account for more than 60% of thoracolumbar fractures. Types of injuries associated with this type of injury may include: endplate impaction, wedge impaction fractures, vertebral body collapse, split fractures and coronal split fractures.

Patients with spine issues all start with collapsing of the disc, which happens due to loss of nutrition as aging occurs, which leads to loss of normal cushioning. Next, the endplates can no longer handle normal stress on the endplates, which leads to microfractures in the adjacent vertebral bodies. The chronic factures in a collapsed or fractured vertebral body may then create a cascade of other conditions in the spine, including (but not limited to) degenerative scoliosis, facet joint subluxation and facet joint degeneration, nerve root compression, and further vertebral body collapse.

Studies have also shown that degenerative disc disease and degenerative scoliosis may be associated with significant pain, mental anguish, anxiety, and functional disability as well as diminished self-perception/mental health and decreased function.

Patients with degenerative disc disease associated with degenerative scoliosis many times have a collapsing foramen on the concave slide of the spine. As this happens the superior facet of the vertebra below slides cephalad and pinches the nerve root in the now narrowed foramen. There is no good minimal surgical treatment with lasting symptom relief available in 2021. Common treatments are decompression without fusion, decompression with limited fusion, and extended (extensive) fusion and reconstruction.

Decompression without Fusion Treatments: A collapsing disc and Vertebral body collapse, which allows the facet from below to come up into the foramen. and cause compression of the nerve root. Some surgeons take a minimalist approach and try to open the foramen by surgically removing parts of the facet joint and some disc to give the nerve root space. While the conservative decompressive procedure without a fusion may be appropriate for selected patients, studies have demonstrated "greater risk of deformity progression, poor outcomes, and higher rates of reoperations" in these cases. It is believed that this is due to failure to address the cause of the narrowed foramen that being subluxation of the facet joints secondary to further disc collapse and further microfractures in the vertebral body leading to further wedging, and the foramen gets narrower again.

Decompression with Limited Fusion Treatments: Decompression with limited fusion is applicable for patients whose symptoms are limited to specific and short segments (1-3 levels), but care must be taken in assessing and correcting the sagittal and coronal alignment. Patients with uncorrected misalignment many times have poor outcomes after decompression with limited fusion. Fusions of any kind in the lumbar spine can many times start a cascade of events by putting increase stress through transferring lumbar spine motion to the unfused segments of the spine resulting in more deterioration of the adjacent levels requiring further treatment which is usually additional fusion. This is referred to in the literature as adjacent level disease.

Extended Reconstruction Treatments: Extended reconstruction (>3 levels) of the lumbar spine has been a foundation of correction for adult degenerative scoliosis. Fusions of this scope starts a cascade of events by putting increase stress through transferring lumbar spine motion to the unfused segments of the spine resulting in more deterioration of the adjacent levels requiring further treatment which is usually additional fusion. Clinical presentation of adjacent segment deterioration, with coronal, sagittal or both deformities above or below causing severe back pain often occur necessitating further additional levels requiring fusion.

Accordingly, there is need for a vertebral implant system and methods of use to treat chronic trauma and fractures resulting in collapsed vertebra and causing back pain and or leg pain that addresses the above shortcomings.

BRIEF SUMMARY OF THE INVENTION

The following summary is included only to introduce some concepts discussed in the Detailed Description below. This summary is not comprehensive and is not intended to delineate the scope of protectable subject matter, which is set forth by the claims presented at the end.

In one example embodiment, a vertebral implant system is provided comprising an upper staple, a lower staple and an adjustable vertical member.

In one example embodiment, a vertebral implant system is provided comprising an upper staple, a lower staple, a vertical member configured to be coupled to the upper staple and the lower staple, and the vertical member comprises an adjustable member. In some embodiments, the adjustable member is configured to be adjusted by one selected from the group consisting of a percutaneous puncture and a small diameter tool or an electromagnetic mechanism. In some embodiments, the adjustable member comprises a ratchet assembly. In some embodiments, the ratchet assembly comprises a thermal ratchet assembly comprising a rack, a pawl configured to engage the rack, the pawl coupled to an adjustable mount, and the adjustable mount comprising a Nitinol wire and a spring. In some embodiments, the ratchet assembly further comprises a radio frequency (RF) receiver configured to receive an RF signal from an electromagnetic transmitter, and the RF receiver configured to communicate the RF signal to an inducer whereby the inducer heats the Nitinol wire. In some embodiments, the adjustable member comprises a turnbuckle assembly. In some embodiments, the turnbuckle assembly comprises a turnbuckle having an engagement element, a first threaded recess and a second threaded recess, a first threaded strut having a first threaded portion configured to be received in the first threaded recess of the turnbuckle, a second threaded strut having a second threaded portion configured to be received in the second threaded recess of the turnbuckle, the first threaded strut having a first anchor eye configured to be secured to an upper staple, the second threaded strut having a second anchor eye configured to be secured to a lower staple, and the engagement element of the turnbuckle configured to be turned by an engagement tool whereby when the first anchor eye is secured to the upper staple and the second anchor eye is secured to the lower staple and the engagement element is turned, a length of the turnbuckle assembly is adjusted. In some embodiments, the adjustable member comprises a keyed turnbuckle assembly. In some embodiments, the keyed turnbuckle assembly comprises a first keyed turnbuckle having a first engagement element and a first threaded recess, a second keyed turnbuckle having a second engagement element and a second threaded recess, a first threaded strut configured to be received in the first threaded recess of the first keyed turnbuckle, a second threaded strut configured to be received in the second threaded recess of the second keyed turnbuckle, the first threaded strut having a first anchor eye configured to be secured to an upper staple, the second threaded strut having a second anchor eye configured to be secured to a lower staple, and the first engagement element and the second engagement element configured to be turned by an engagement tool whereby when the first anchor eye is secured to the upper staple and the second anchor eye is secured to the lower staple and the engagement tool is turned to engage the first engagement element and the second engagement element, a length of the keyed turnbuckle assembly is adjusted.

In one example embodiment, a vertebral implant system is provided comprising an upper staple, a lower staple, a vertical member configured to be coupled to the upper staple and the lower staple, and the vertical member further comprises a plate. In some embodiments, the plate further comprises an offset guide protruding from an inner surface of the plate. In some embodiments, the offset guide defines an offset dimension component to define an angle of a sagittal correction of a vertebral body after an anterior vertebral body osteotomy performed through an anterior, lateral, or oblique approach to the vertebral body. In some embodiments, the plate is configured with a curve to define an angle of a coronal correction of a vertebral body.

In one example embodiment, a screw plate alignment system is provided comprising a bone screw comprising a threaded portion and a tip portion, a plate comprising one or more through hole configured to receive the threaded portion and the tip portion, and a locking element configured to frictionally anchor the tip portion of the bone screw in the one or more through hole. In some embodiments, the screw plate alignment system further comprises an exterior surface of the tip portion is a roughened surface. In some embodiments, the screw plate alignment system further comprises a securing element configured to frictionally engage an exterior surface of the tip portion of the bone screw and an interior surface of the locking element whereby the tip portion of the bone screw is further anchored in the one or more through hole. In some embodiments, the screw plate alignment system further comprises a longitudinal slit in the locking element and a longitudinal slit in the securing element whereby a circumference of an inner surface of the locking element and a circumference of an inner surface of the securing element are reduced to increase a frictional compression force on the tip portion of the bone screw.

In some embodiments, the vertebral implant device is configured to be positioned as one of an intervertebral implant device positioned between a first and a second vertebral body, and an intravertebral implant device positioned between a first portion and a second portion of a single vertebral body.

In some embodiments, the vertebral implant device is configured to correct both a coronal and a sagittal deformity of a vertebral body after an anterior vertebral body osteotomy performed through an anterior, lateral, or oblique approach to the vertebral body.

In some embodiments, the vertical member is an adjustable member configured to be adjusted by (a) a percutaneous puncture and a small diameter tool or (b) an electromagnetic mechanism.

Other objects, features, and advantages of the techniques disclosed in this specification will become more apparent from the following detailed description of embodiments in conjunction with the accompanying drawings.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 4C, 4D and 4E showing a vertical member comprising a bracket;

Figure 6A:
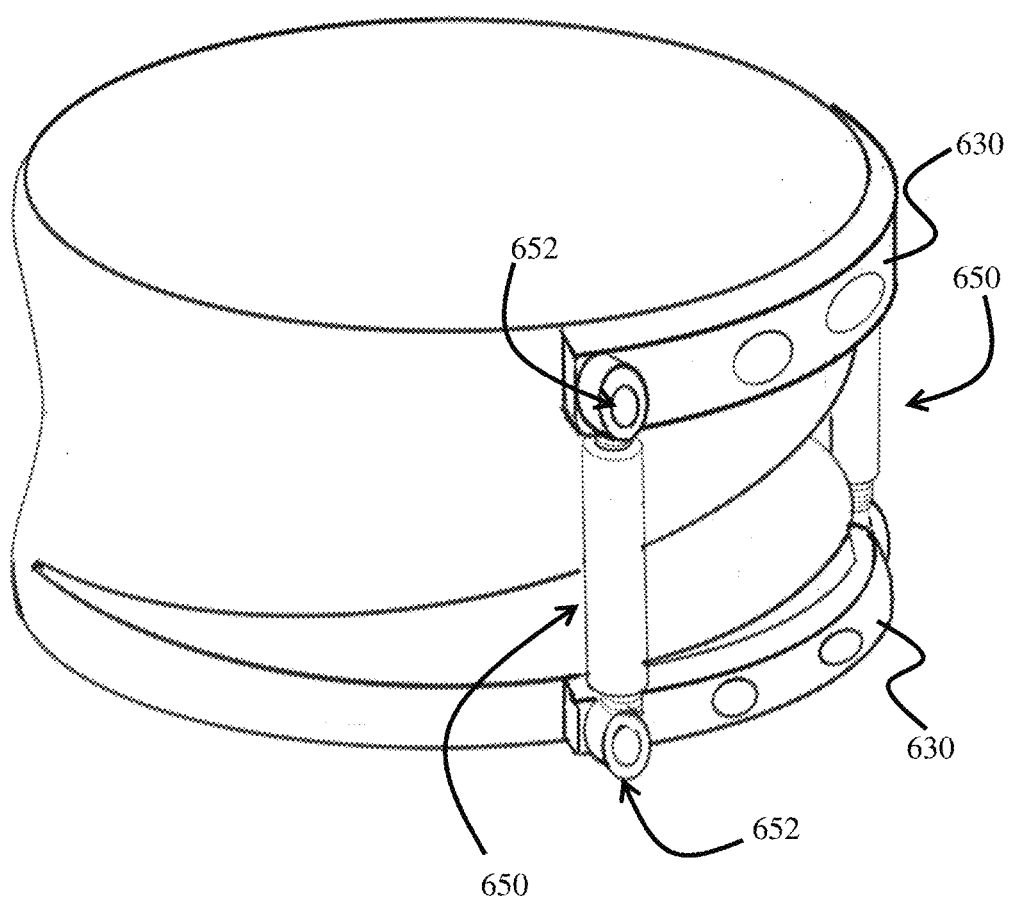
Figure 7A:
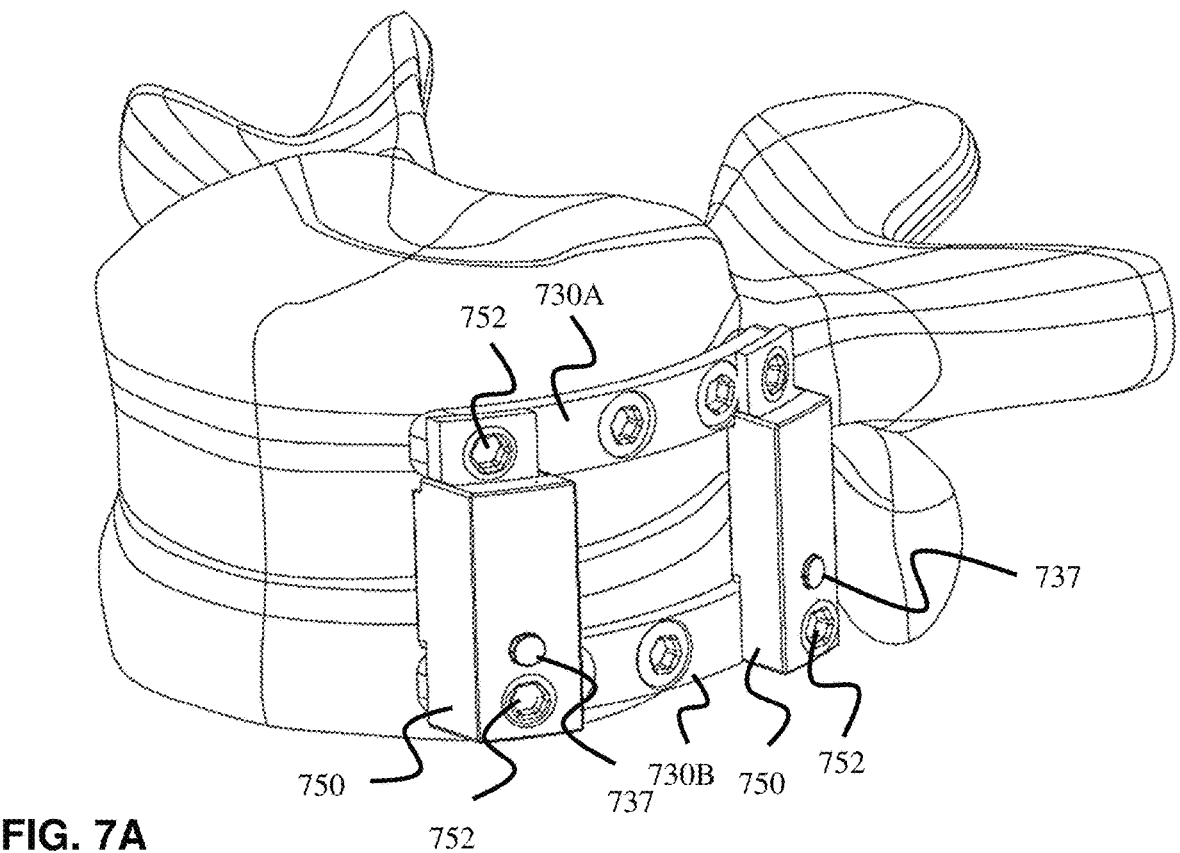
Figure 7B:
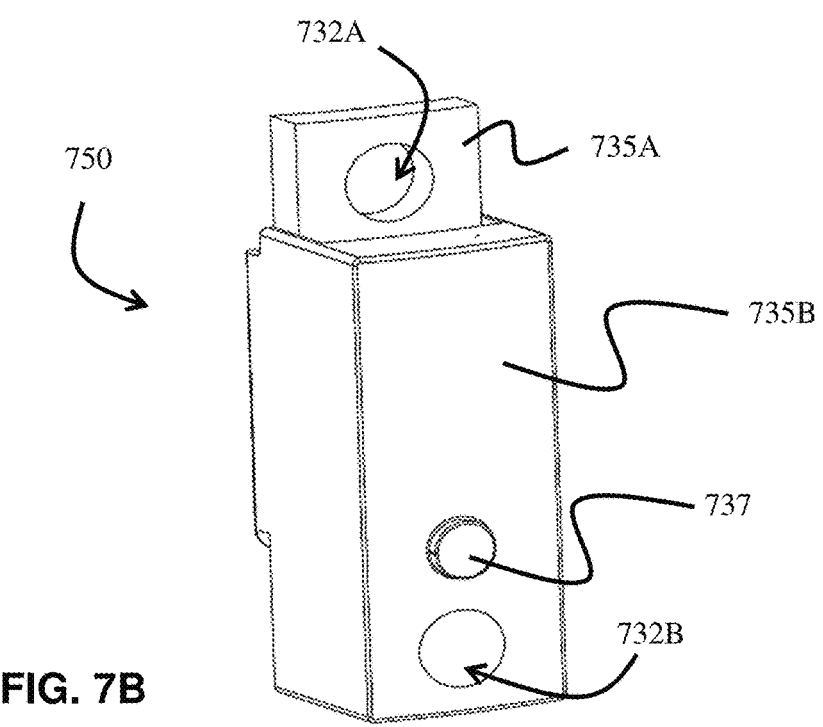
Figure 7C:
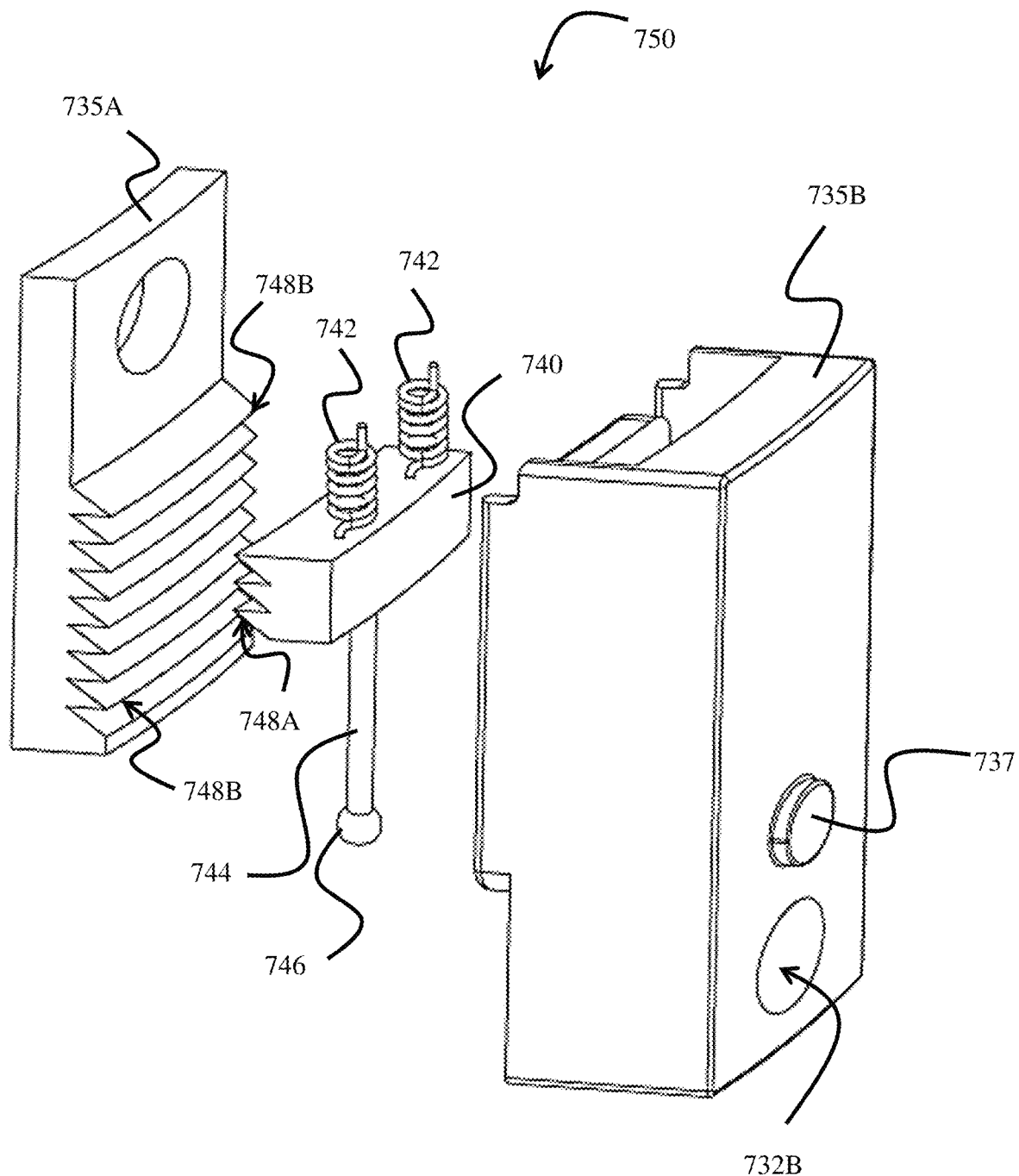
Figure 7D:
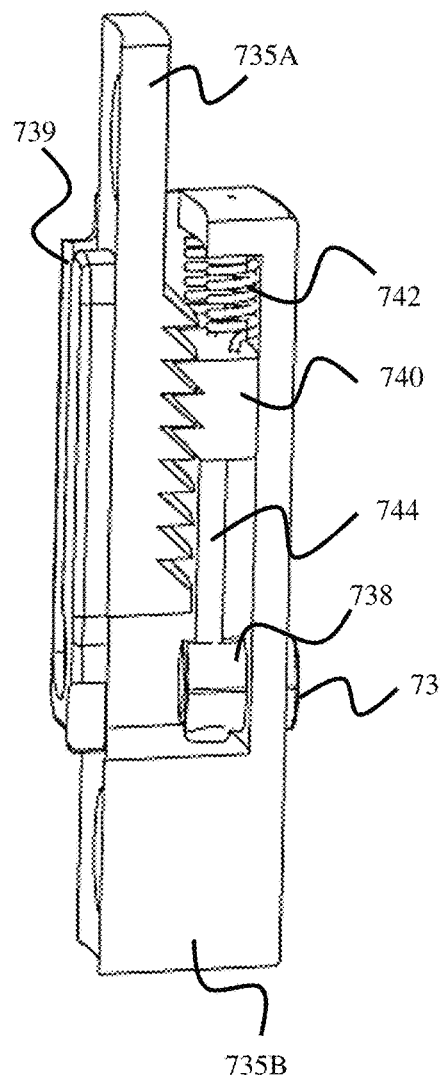
Figure 7E:
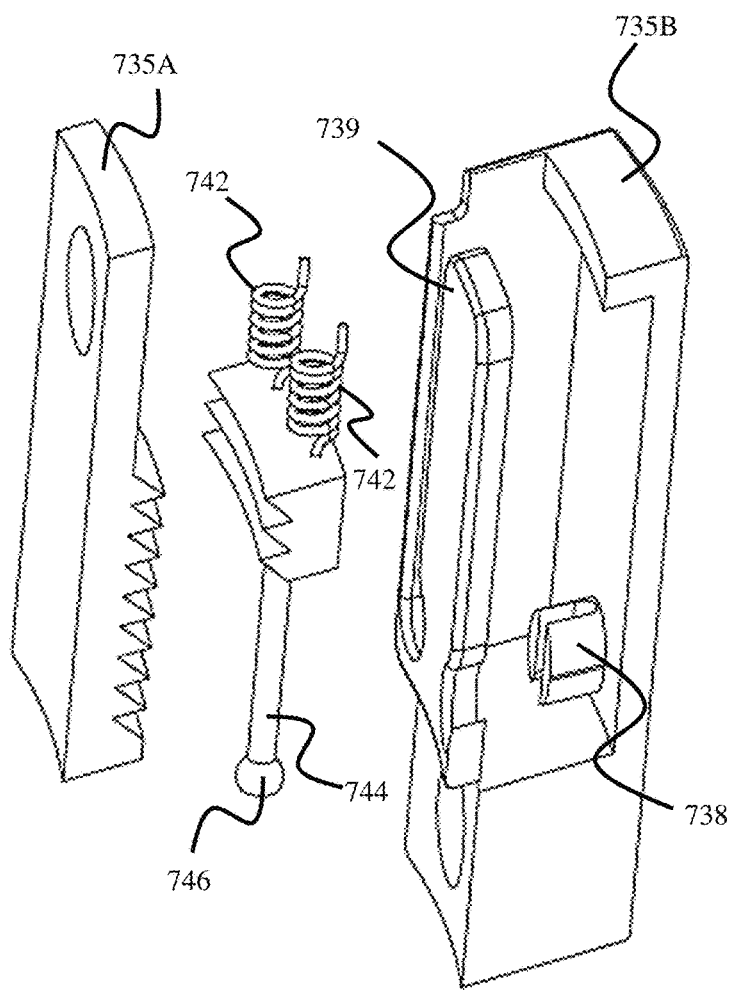
Figure 8A:
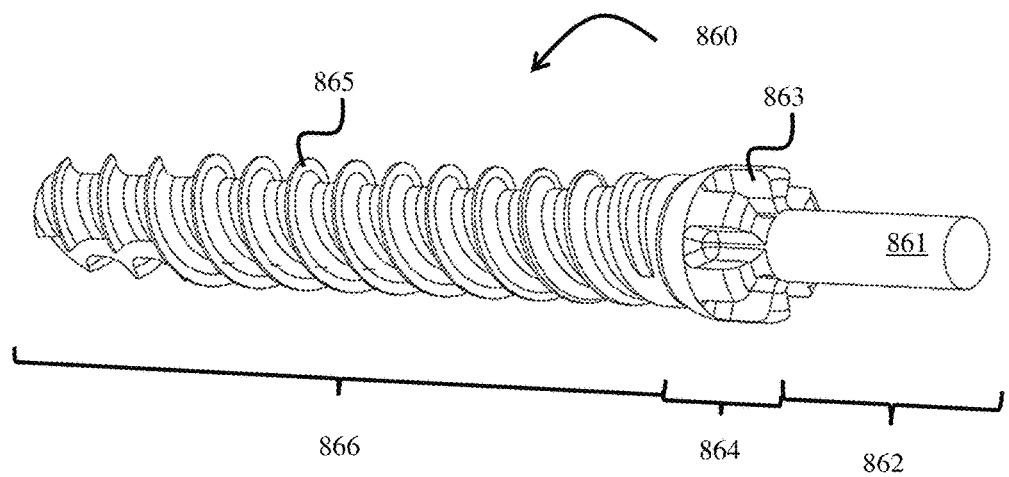
Figure 8B:
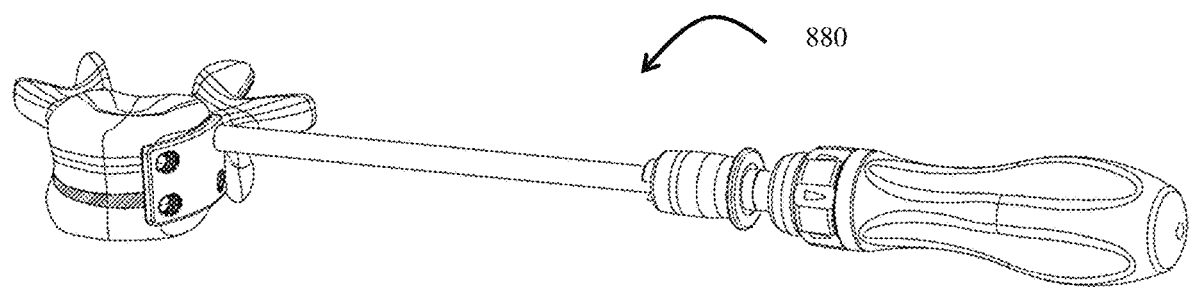
Figure 9A:
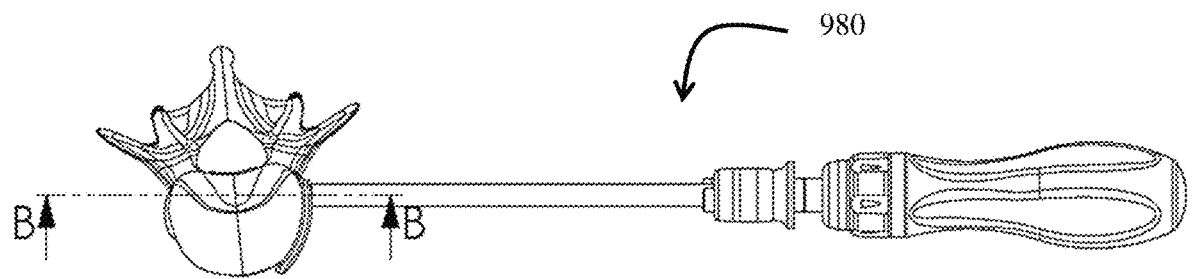
Figure 9B:
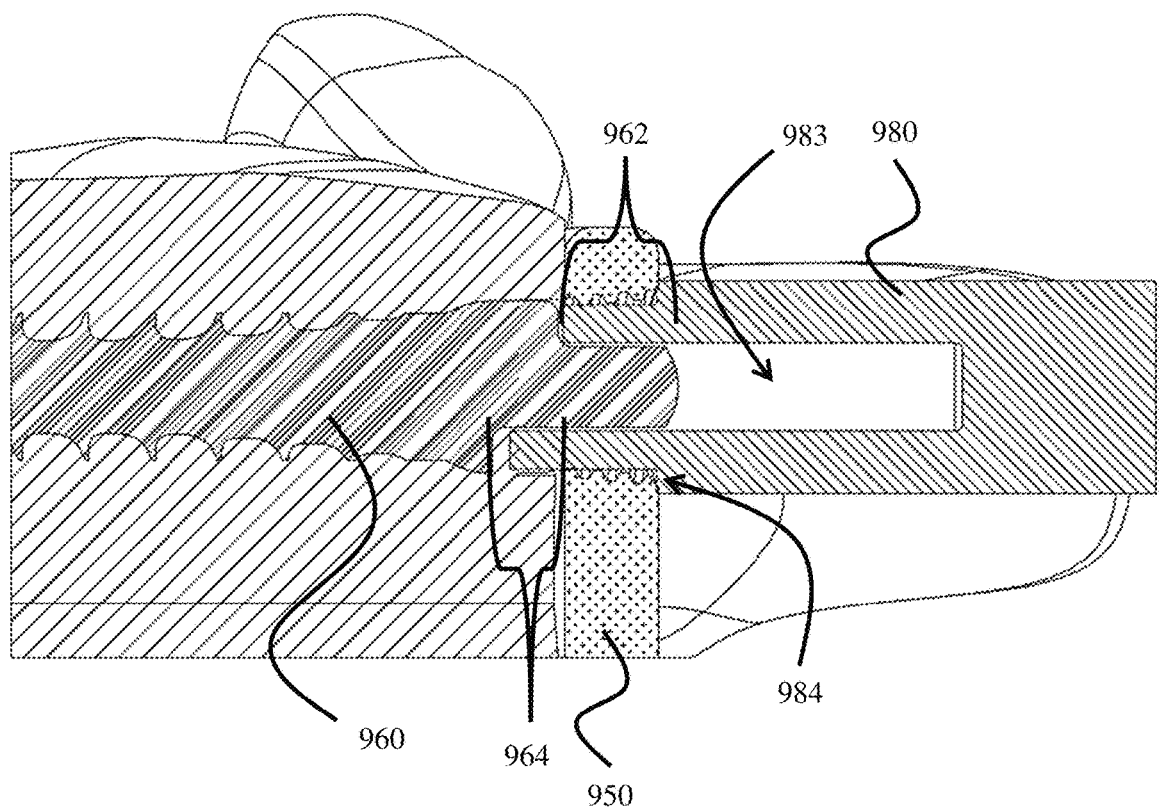
Figure 9C:
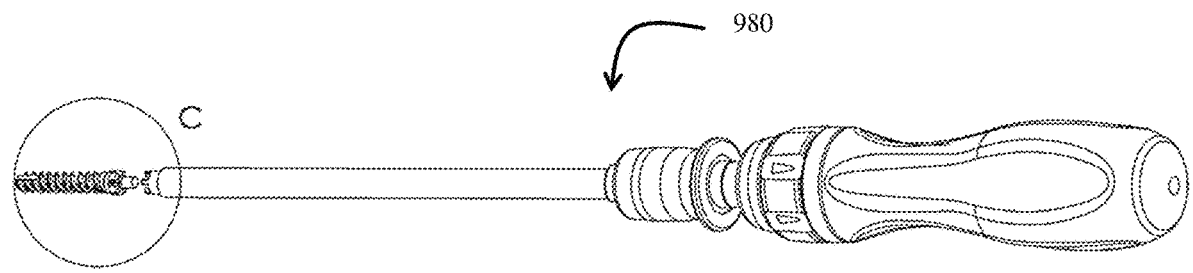
Figure 9D:
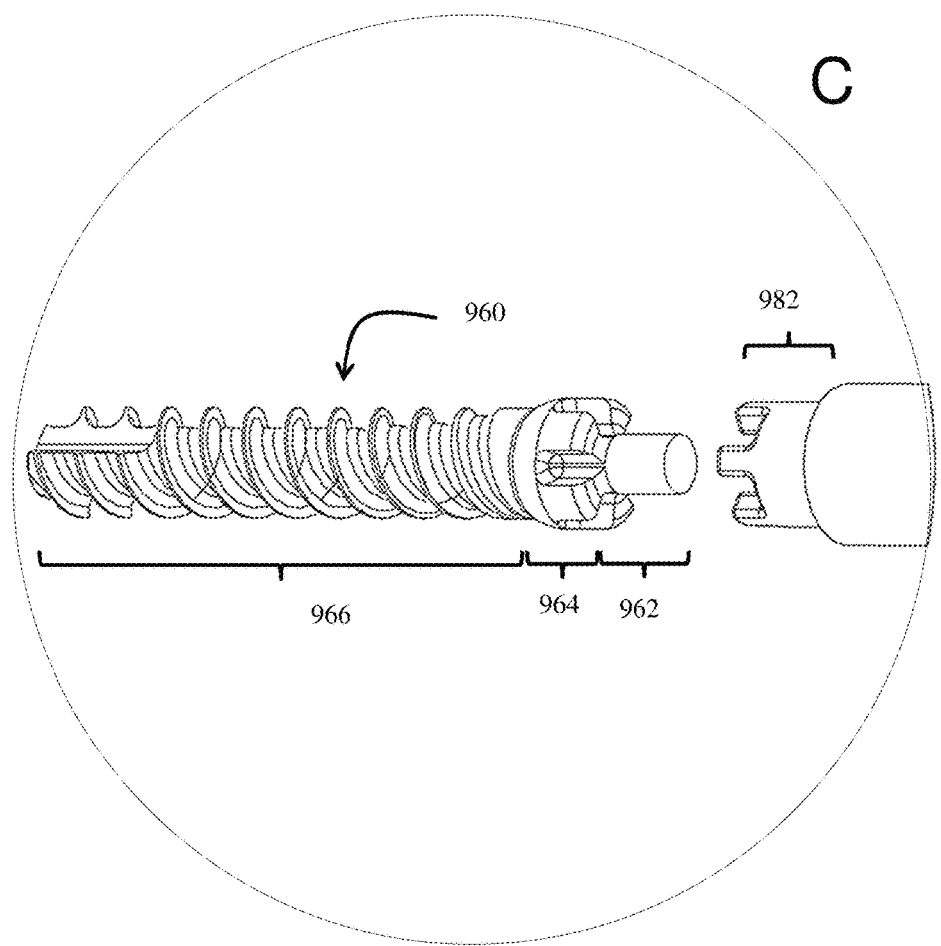
Figure 9E:
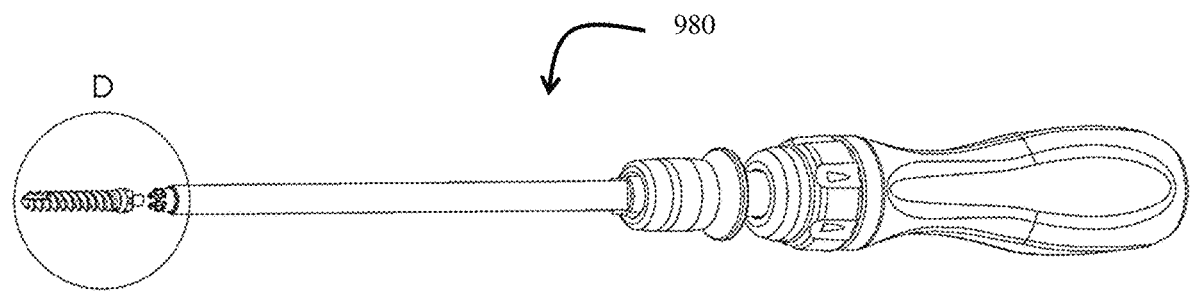
Figure 9F:
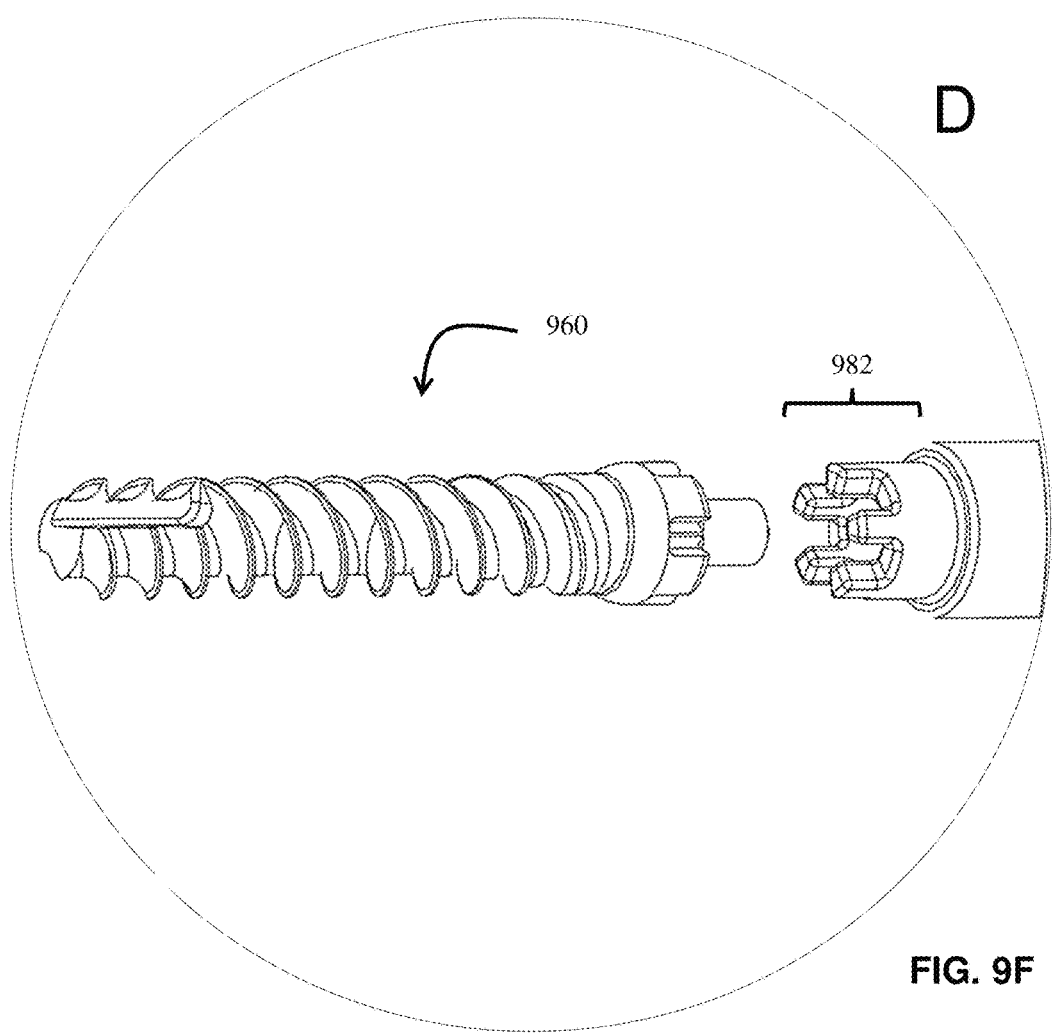
Figure 10A:
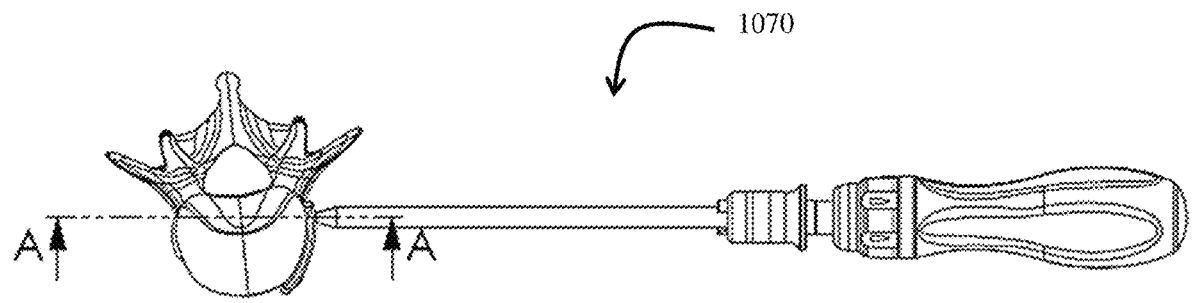
Figure 10B:
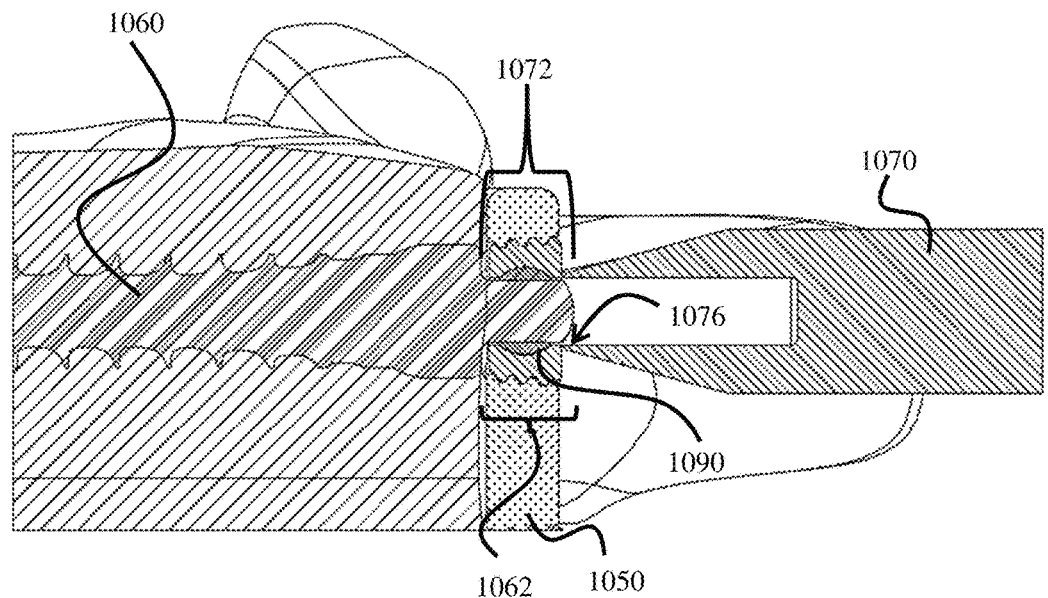
Figure 10C:
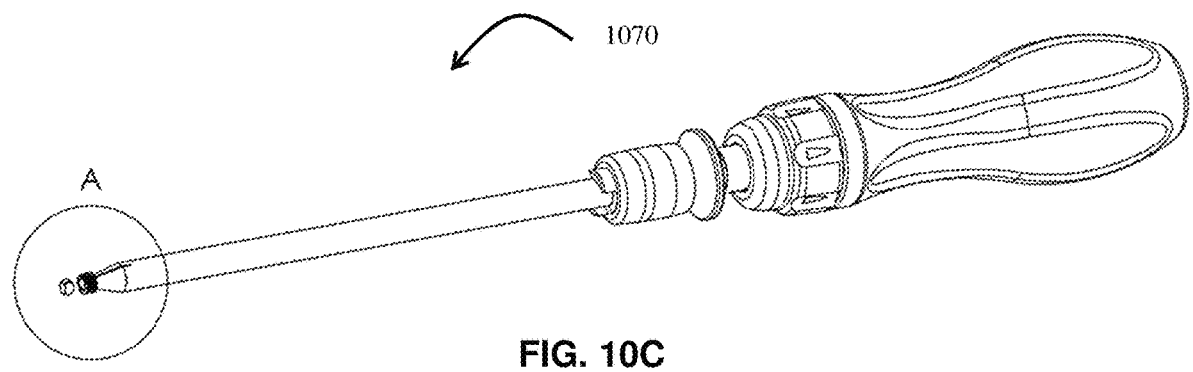
Figure 10D:
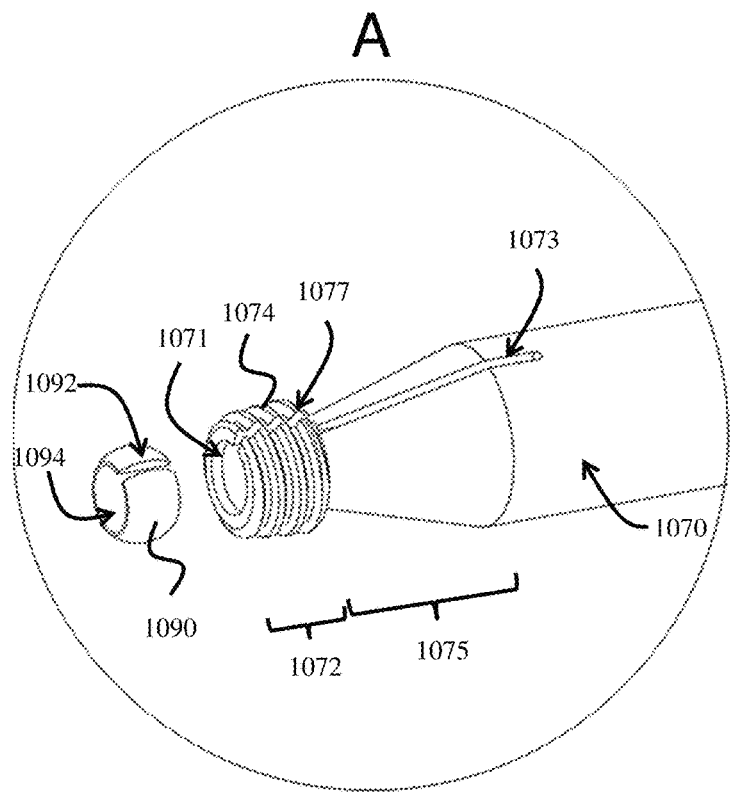

5C showing another exploded view of another embodiment of the vertebral implant system;

FIGS. 6A-6C illustrate other example embodiments of a vertical member comprising an adjustable member with FIG. 6A showing the vertebral implant with the adjustable member coupled to the implant, FIG. 6B showing details of an adjustable member, and FIG. 6C illustrates details of another example embodiment of a vertical member;

FIGS. 7A-7E illustrate another example embodiment of a vertebral implant with FIG. 7A showing the vertebral implant with the adjustable member, FIG. 7B showing details of an example embodiment of a thermal ratchet assembly as the adjustable member, FIG. 7C showing an exploded view of the adjustable member, FIG. 7D showing a cut away view of the adjustable member and FIG. 7E showing an exploded cut away view of the adjustable member;

FIGS. 8A and 8B illustrating an example embodiment of a tipped bone screw with FIG. 8A showing the tipped bone screw and FIG. 8B showing a screw driver engaged with a tipped bone screw;

FIGS. 9A-9F illustrate an example embodiment of a screw driver with FIG. 9A showing the screw driver engaged with a tipped bone screw, FIG. 9B showing a cross section of the screw driver engaged with the tipped bone screw in a vertebral body, FIG. 9C showing the screw driver positioned to be engaged with a tipped bone screw, FIG. 9D showing details of the screw driver and the tipped bone screw, FIG. 9E showing another view of the screw driver positioned to be engaged with a tipped bone screw and FIG. 9F showing another view of details of the screw driver and the tipped bone screw; and FIGS. 10A-10D illustrate an example embodiment of a lock driver with FIG. 10A showing the lock driver engaged with a tipped bone screw, FIG. 10B showing a cross section of the lock driver engaged with the tipped bone screw in a vertebral body, FIG. 10C showing an exploded view of the lock driver and securing element and FIG. 10D showing details of the lock driver and the securing element.

DETAILED DESCRIPTION OF THE INVENTION

COPYRIGHT NOTICE: A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. The following notice applies to any data as described below and in the drawings hereto: Copyright © 2020-2022, NOFUSCO Corporation, All Rights Reserved.

Vertebral implant systems and methods of use will now be described in detail with reference to the accompanying drawings. Notwithstanding the specific example embodiments set forth below, all such variations and modifications that would be envisioned by one of ordinary skill in the art are intended to fall within the scope of this disclosure.

The implant device generally uses the shape of implant components, such as staple tines, to alter the alignment of skeletal components of a mammalian body. Some embodiments use the adjustability of implant components to also alter alignment of skeletal components.

Although embodiments of the implant device may be positioned from different planes relative to the vertebral body, some embodiments are specifically configured to be inserted and secured from a lateral or an oblique approach angle. These approach angles are particularly beneficial because they reduce the risk of complications from more traditional anterior approach procedures. Insertion from lateral and oblique angles makes it easier to avoid blood vessels, the peritoneal cavity and abdominal muscles during the insertion procedure. This lowers the risk that may be caused by injury to these organs and also minimizes or reduces the need for other specialists, such as vascular surgeons or general surgeons, which may otherwise be required to assist in the procedure.

One particular oblique approach, also called the anterior-to-psoas (ATP) approach, may be used to access the vertebral body and implant the device. With this ATP approach, surgical access is provided to the vertebral body which can sometimes alleviate the need for an additional vascular or general surgeon. With this approach, an oblique incision is made on the patient and abdominal muscles and the retroperitoneal space are bluntly dissected to expose the psoas muscle. The psoas muscle or psoas tendon is retracted posteriorly to define the surgical corridor and expose the spine and vertebral body for the surgery.

Figure 1A:
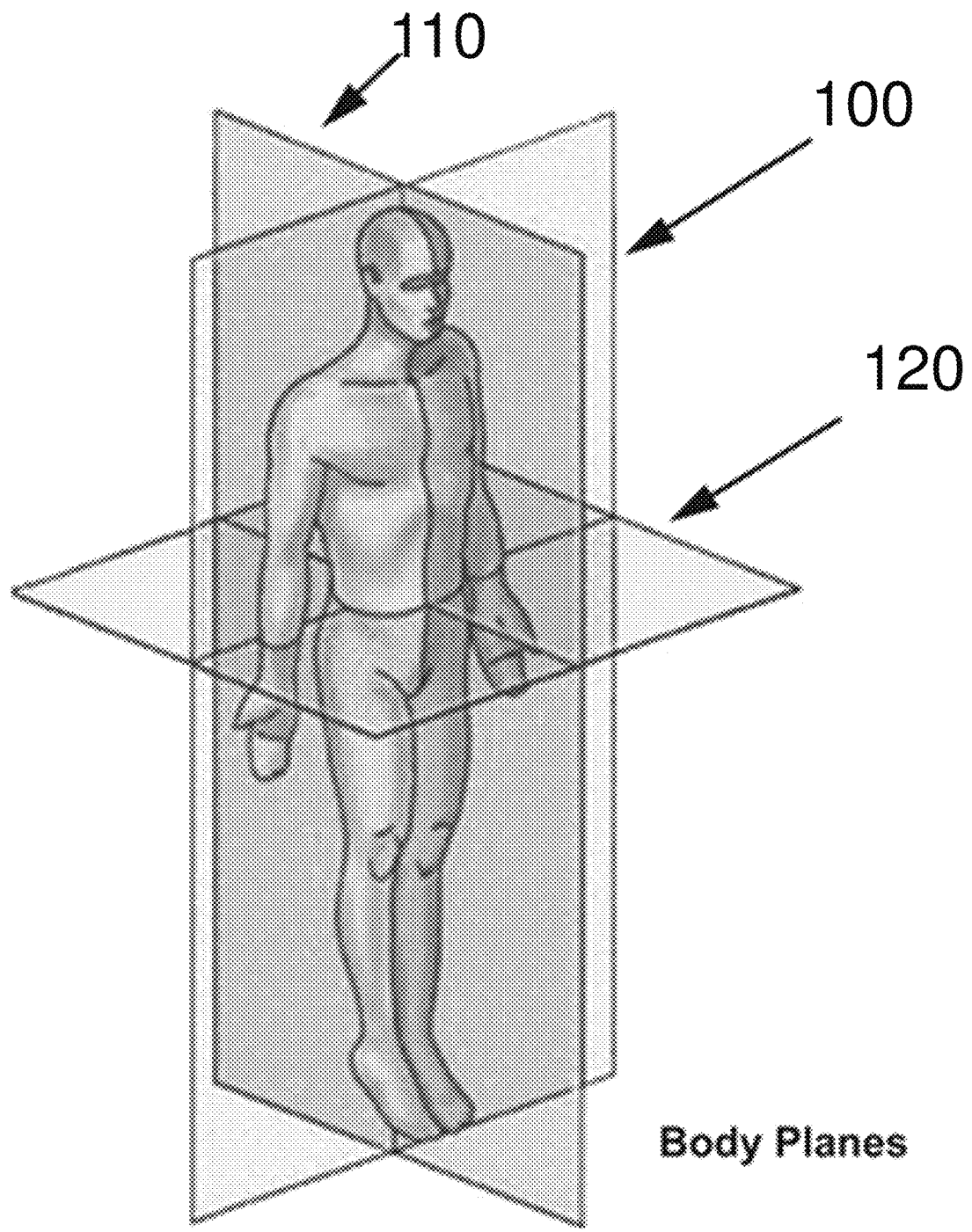
FIG. 1A shows the sagittal, coronal and transverse planes of the human body.

Referring to FIG. 1A showing the sagittal 110, coronal 100 and transverse 120 planes of the human body, embodiments may be used to correct alignment of the spine in the sagittal (110) and coronal (100) planes.

Figure 1B:
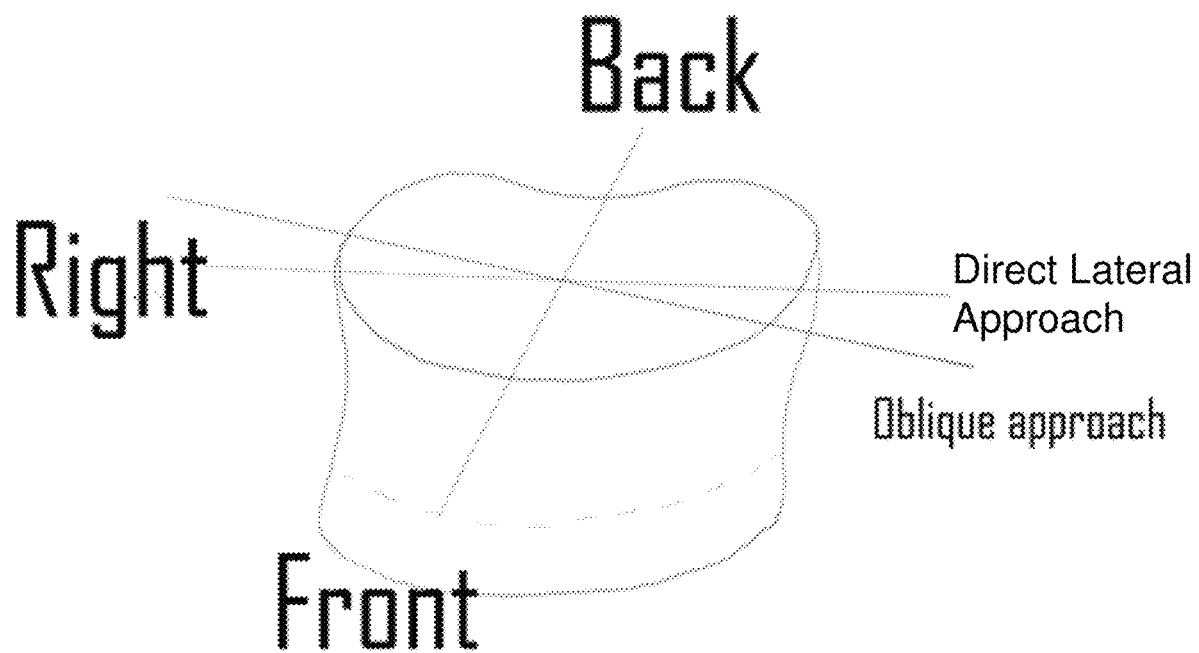
FIG. 1B illustrates the different axis and placement approaches used with example embodiments of the vertebral implant system.

Referring to FIG. 1B, the implant system may be inserted and positioned at and from different angles relative to the vertebral body. The placement and configuration of the implant components dictate the different alignment surface angles of the vertebral bodies. For example, embodiments of the vertebral implant system may be implanted through anterior (front), oblique or lateral (left/right) approaches.

Figure 1C:
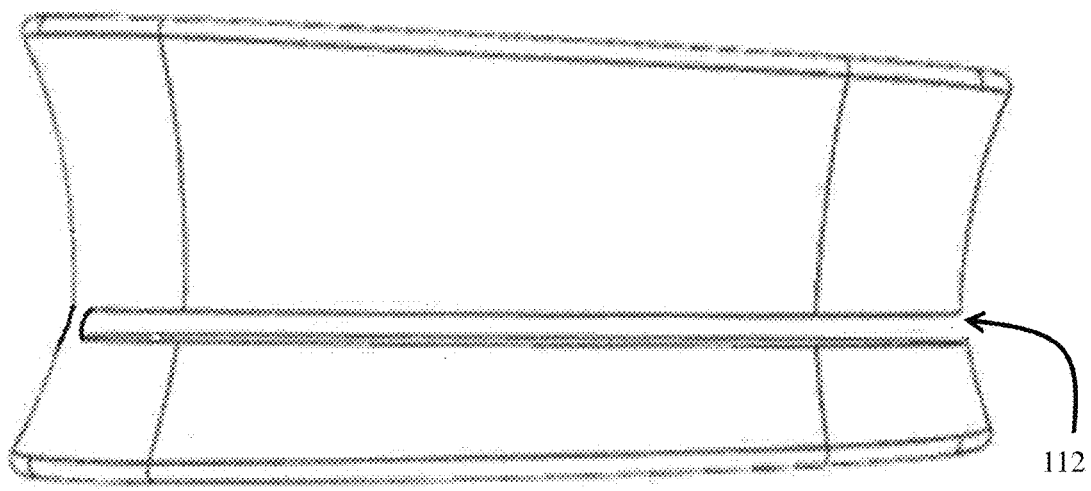
FIG. 1C illustrates an example osteotomy of the vertebral body.

The implant system is generally used in conjunction with an osteotomy made through the vertebral body inferior to the pedicle as shown in FIG. 1C. As shown, the osteotomy 112 is typically cut inferior to the inferior aspect of the pedicle.

In some embodiments, the implant system functions as an exoskeleton, primarily positioned outside of the vertebral body. The main interface of the implant system is at the end plate and the apophyseal ring of the vertebral body.

In some embodiments, the implant system preserves the spinal vascular system.

In some embodiments, the configuration of the implant system allows bone fusion within the vertebral body after placement such that the implant system may be a temporary fixation and adjustment device.

In some embodiments, the implant system is configurable. For example, some embodiments of the implant system may be configured to provide different alignments to vertebral bodies and the spine. For example, some embodiments of the implant system may provide configurable dimensions such as different height and angles to provide different sagittal and coronal angle when positioned in the vertebral body.

In some embodiments, the configurability of the implant system is provided by adjustable components. For example, the implant system may provide adjustable components that provide adjustable dimensions such as adjustable implant dimensions and implant angles to provide different sagittal and coronal angles when positioned in the vertebral body. In some embodiments, the adjustability of the implant system may be provided while the implant system is positioned in the vertebral body.

In some embodiments, provisions may be made to couple the implant system to other constructs as rod systems and plate systems.

In some embodiments, the vertebral implant device and system may be used as either an intervertebral implant device and implant system between two vertebrae or as an intravertebral implant device and implant system between two portions of a single vertebral body.

One Example Embodiment of the Vertebral Implant System:

In an example embodiment, the vertebral implant system comprises a vertebral implant device. For illustration purposes and not for limitation, one example embodiment of the vertebral implant device is shown in FIGS. 3A-3C.

Figure 3A:
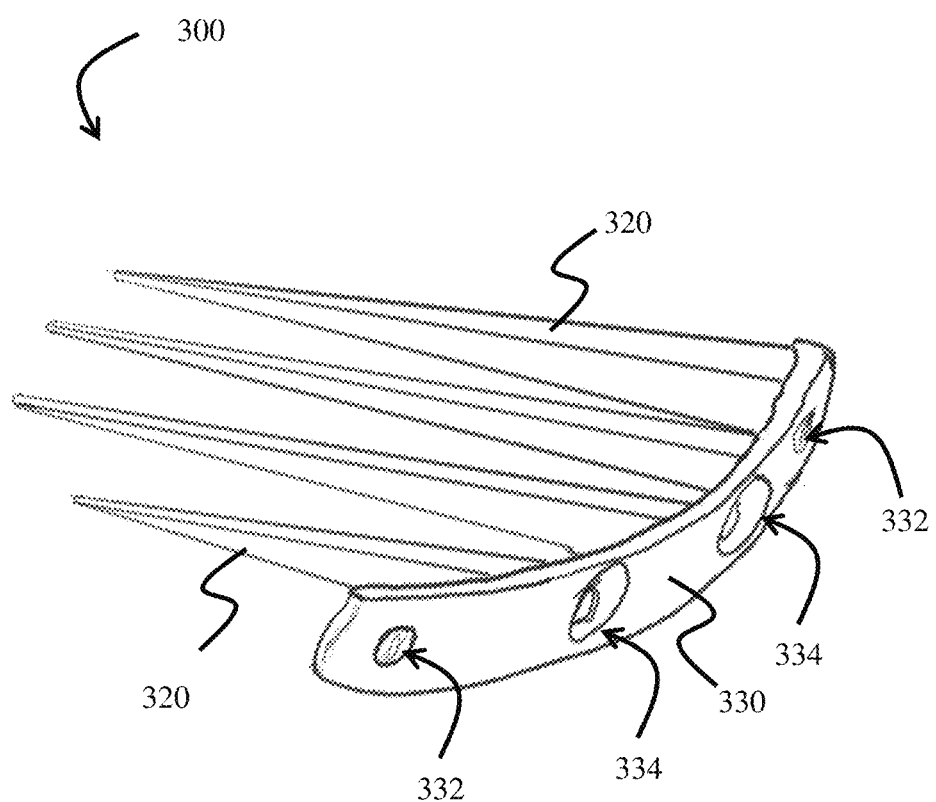
FIGS. 3A-3C show different views of an example embodiment of a staple for a vertebral implant system.

As shown in the embodiment of FIG. 3A, the vertebral implant system generally comprises a vertebral implant device comprising a staple 300 having one or more staple tines 320 extending from a staple plate 330. The configuration of the multiple staple tines 320 with spacing between them is to allow ample blood supply to still reach the entire vertebral endplates both superior and inferior of the vertebral bodies when the staple 300 is positioned in the vertebral body. In addition, the spacing allows ample blood supply to continue to provide nutrients to the intervertebral disc. As shown, the staple tines 320 generally extend from the staple plate 330 and the staple plate 330 generally couples the staple tines 320 together. The staple tines 320 are configured to cross the vertebral body in approximation to the end plate and apophyseal ring. In some embodiments, the staple tines 320 may be configured to be bi-cortical. The positioning of the staple tines 320 in the vertebral body, and the positioning of the upper staple relative to the lower staple after implanting define an offset dimension quantifying the alteration made to the end plate planes of the vertebral body. The offset dimension may generally be equal to the gap between the inner surfaces of the vertebral member opened with a partial or through osteotomy.

Figure 3B:
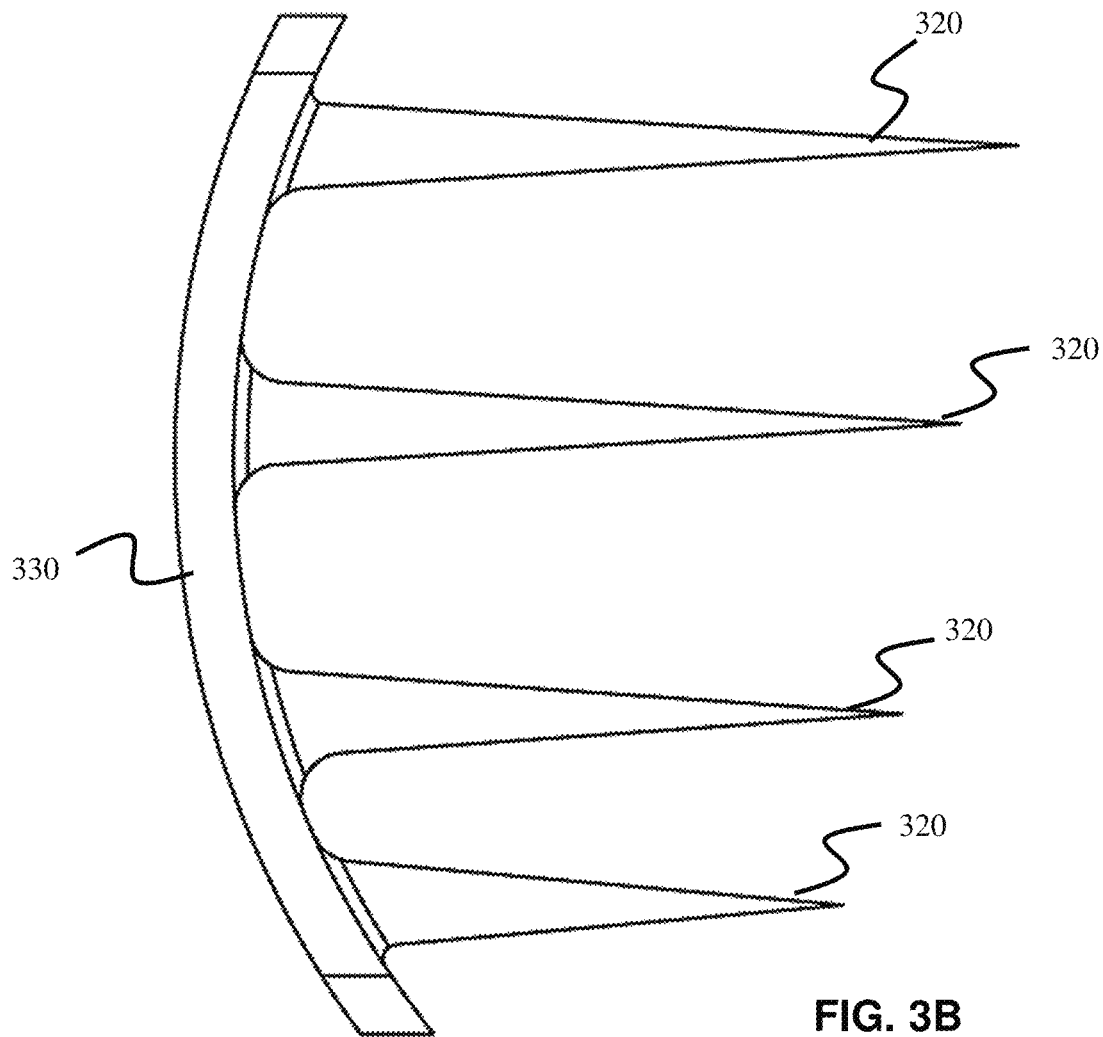

As shown in the top view of FIG. 3B, each of the staple tines 320 are generally dimensioned and spaced to allow a blood supply to flow between the staple tines 320 and reach the entire vertebral endplates both superior and inferior of the vertebral bodies when the implant is positioned in the vertebral body.

Figure 3C:
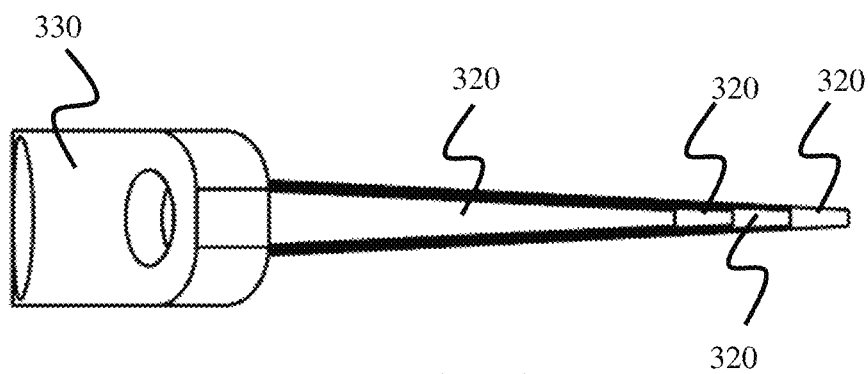

As shown in the side view of FIG. 3C, each of the staple tines 320 define a generally flat/planar profile in the plane consistent with the osteotomy. The profile defined by the staple tines 320 may also be altered to make corresponding alterations in the end plate planes. Reinforcement of the staple tines 320 may be added where they couple to the staple plate 330.

Figure 3D:
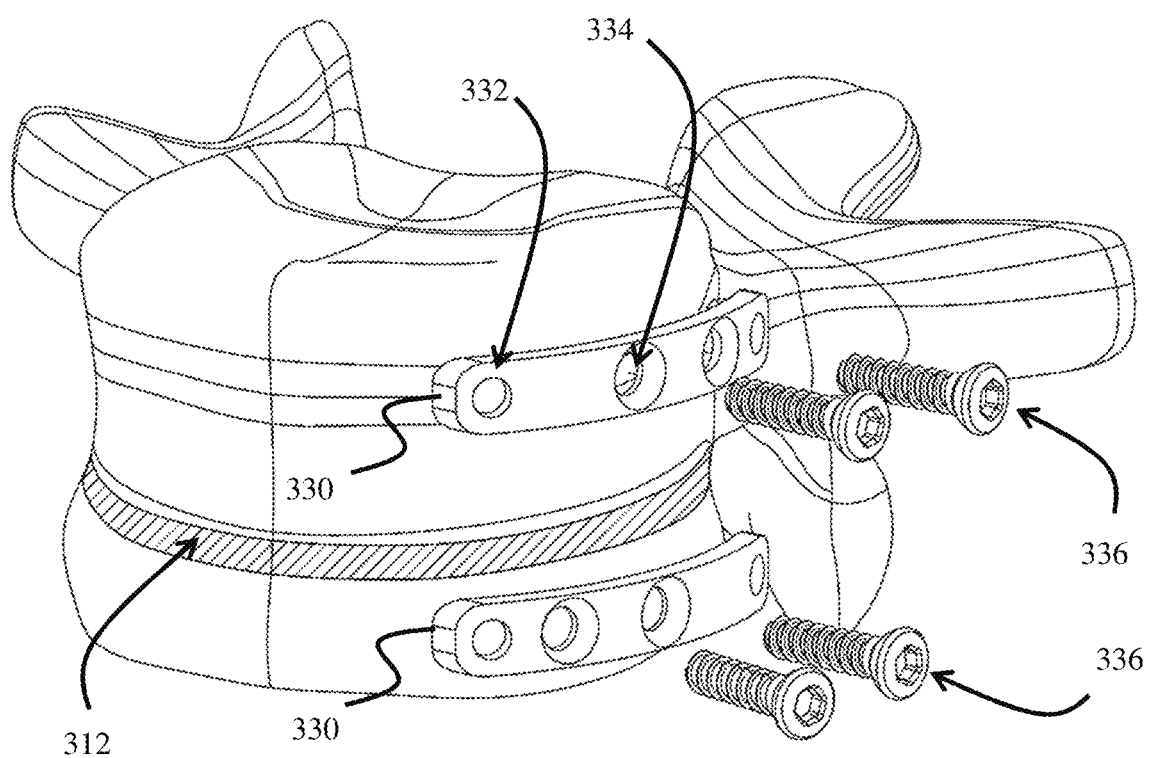
FIG. 3D shows an example embodiment of a staple as positioned in a vertebral body with staple screws configured to anchor the staple to the body.

As shown in FIG. 3D, the staple plate 330 may also provide the elements to secure the implant device to the vertebral body. As shown, one example element to secure the implant device to the vertebral body may be through holes 334 to accept an anchor such as a bone screw 336. The staple plate 330 may also have elements to secure the implant device to other system components. As shown, one example element to secure the implant device to other system components may comprise holes 332 that may receive a coupling element like a screw to secure an element such as a plate (see FIG. 4A) or bracket (see FIG. 4C) to the implant device. In some embodiments, a screw may be used to anchor the staple plate 330 to the vertebral body and a tulip screw head may be used to attach a longitudinal rod or cord between multiple vertebrae. As shown, one staple is secured to the vertebral body above the osteotomy 312 and one staple is secure below the osteotomy 312.

Figure 2:
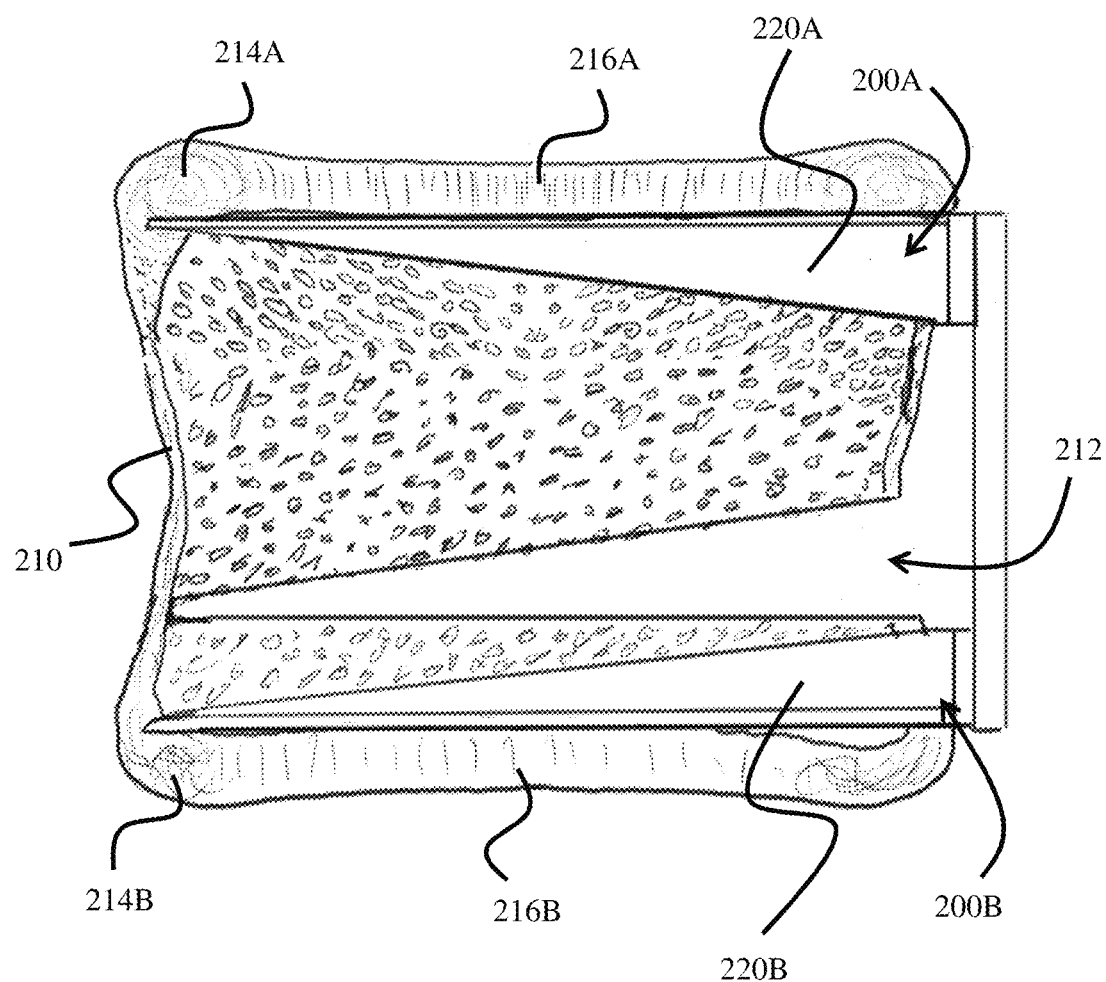
FIG. 2 illustrates an example embodiment of the vertebral implant positioned in a vertebral body.

As shown in FIG. 2, the staples 200A and 200B are configured to have the corresponding staple tines 220A and 220B secured beneath the apophyseal ring 214A and above apophyseal ring 214B of the vertebral body 210. FIG. 2 illustrates an example embodiment of using multiple staples (200A and 200B) with one set of staple tines (220A) positioned under the superior end plate 216A and one set of staple tines (220B) positioned above the inferior end plate 216B. FIG. 2 illustrates an anterior view with the osteotomy 212 and staple tines 220A and 220B positioned to alter the spine alignment in the coronal plane to correct deformities such as scoliosis. Similarly, the osteotomy 212 may be made from, and the staples 200A and 200B with corresponding staple tines 220A and 220B may be positioned from, oblique or anterior angles to alter the spine in the sagittal plane to correct deformities such as lordosis or kyphosis.

Figure 4A:
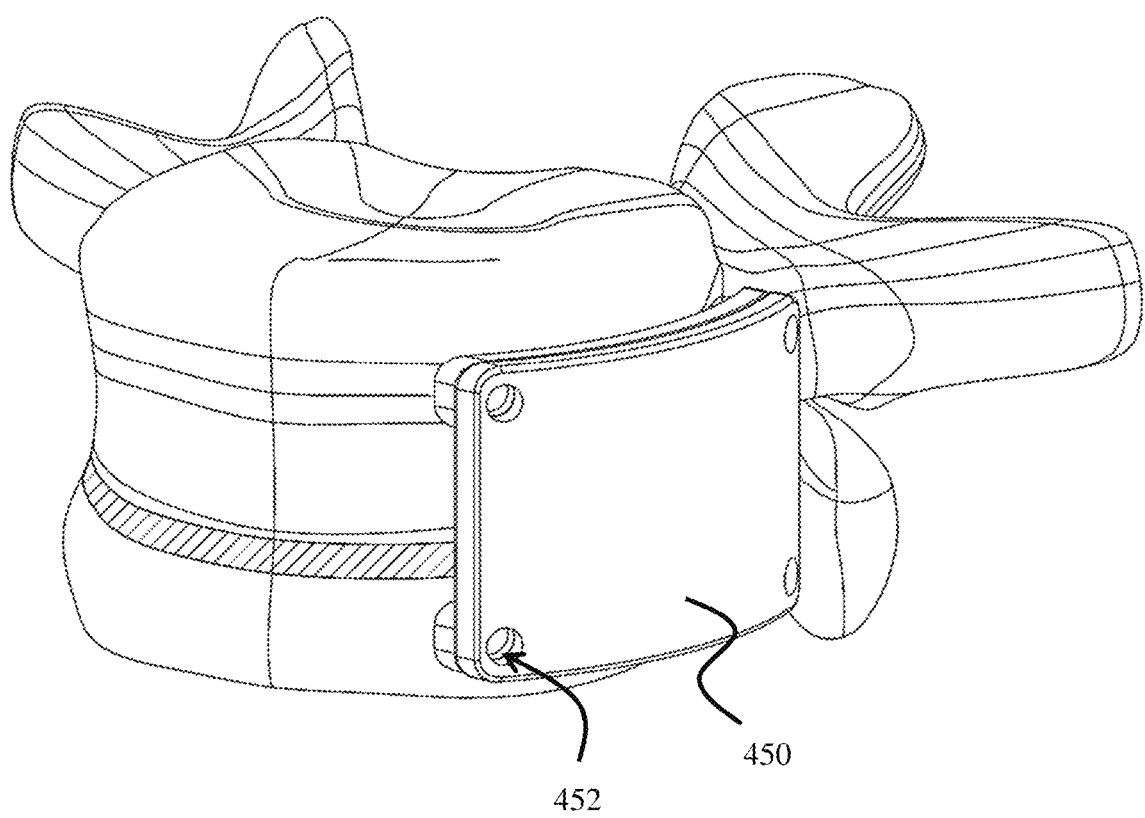
FIGS. 4A-4E illustrate examples of a vertical member with FIGS. 4A and 4B being a vertical member comprising a plate.
Figure 4B:
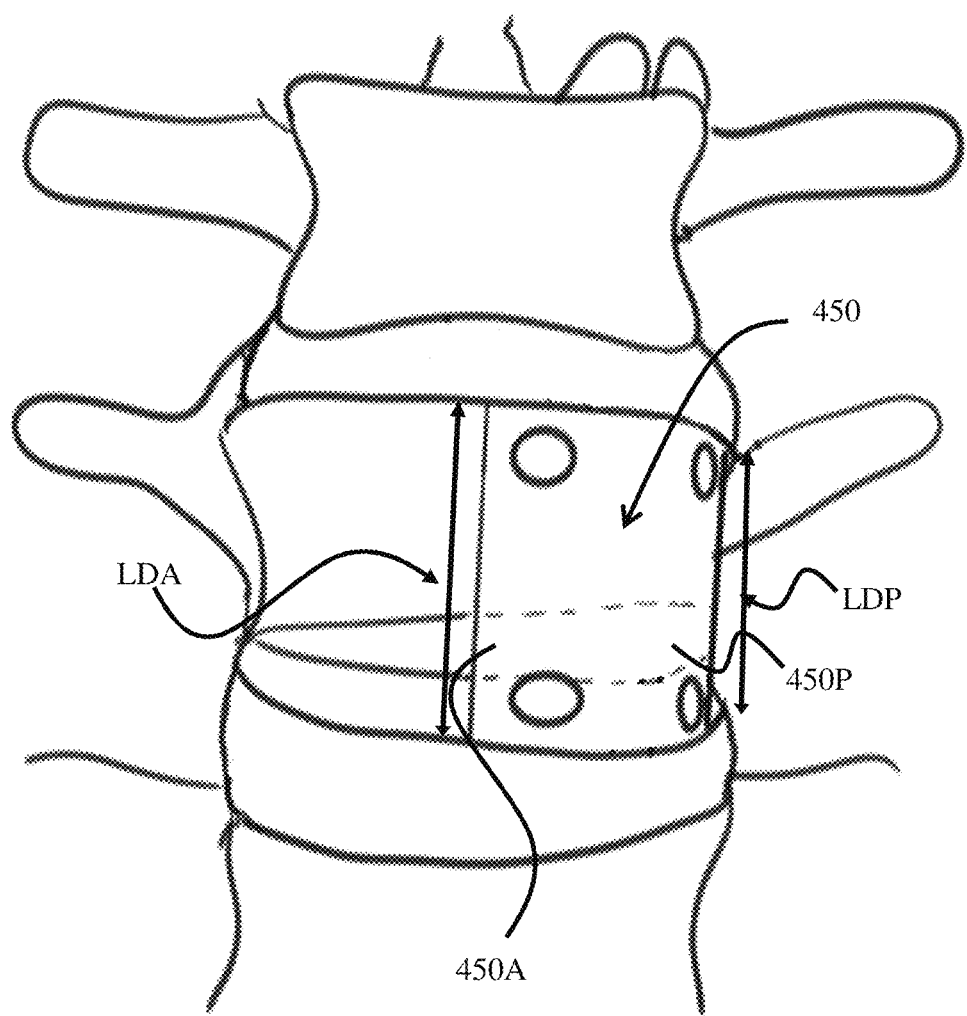
Figure 4C:
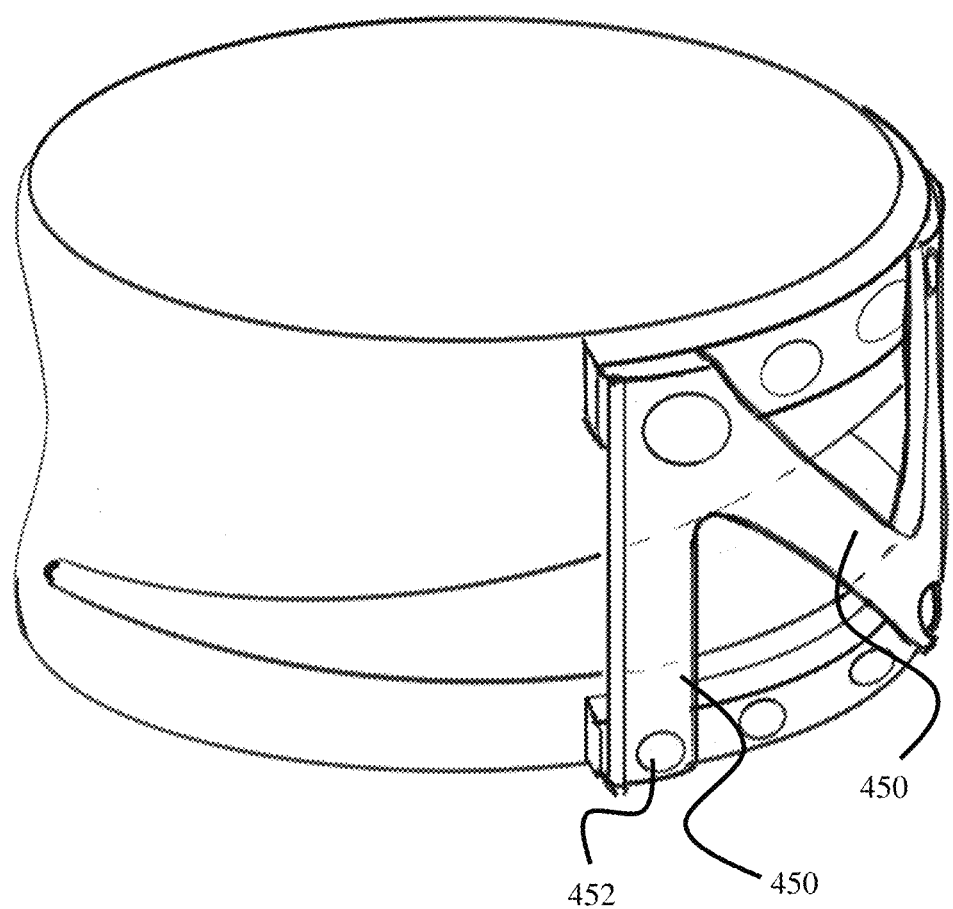
Figure 4D:
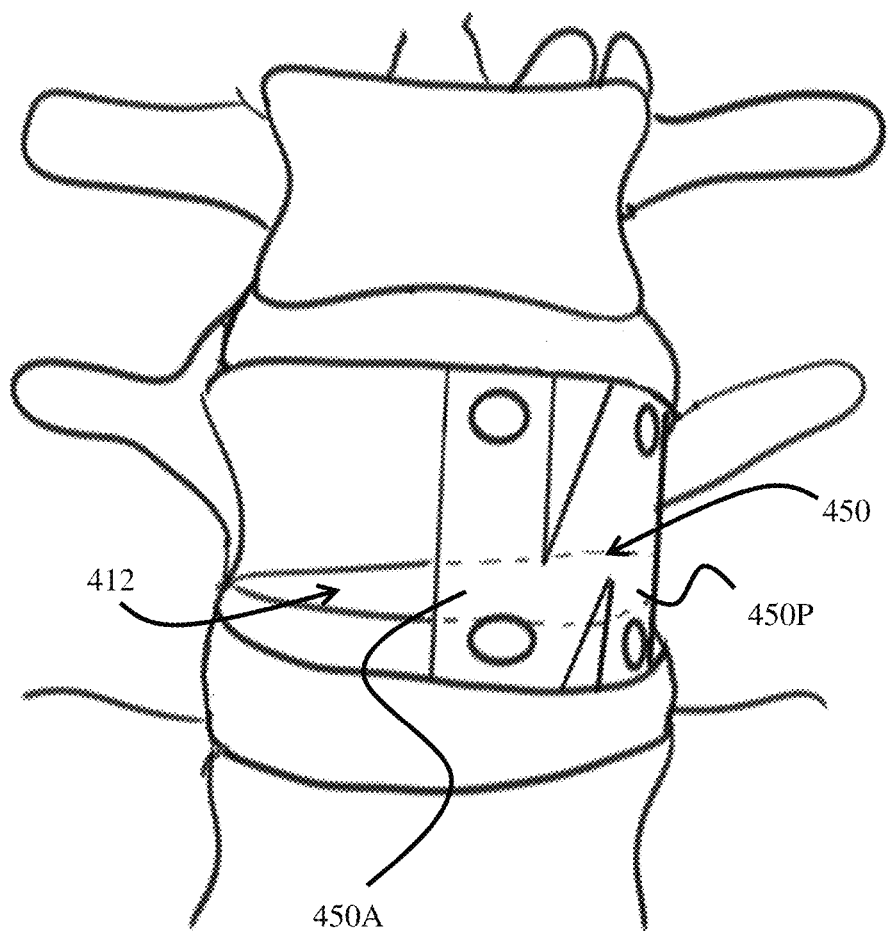
Figure 4E:
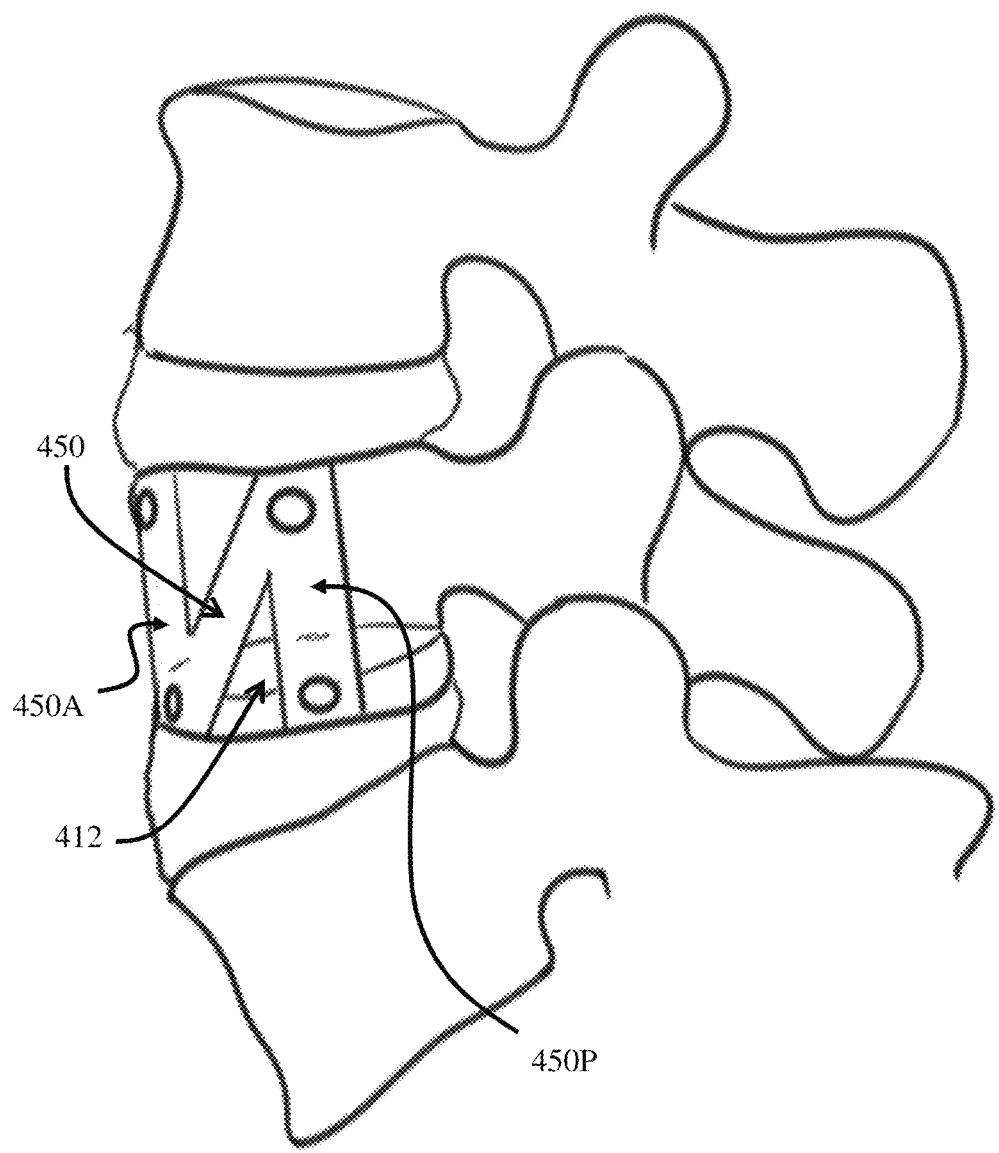

Referring to FIGS. 4A-4E, the implant system may further comprise a vertical member 450. The vertical member 450 generally functions to stabilize the implant device and fix the offset gap formed by the osteotomy as the offset dimension. Fixing, or securing this gap at a particular dimension, fixedly corrects the alignment of the vertebral body surface planes. The vertical member 450 may be one of multiple different sized members to provide configurability to the implant system. The vertical members 450 may have different heights to correct different degrees of coronal plane wedging and they may also be different heights anterior versus posterior to adjust for sagittal plane vertebral body deformity. As shown in FIG. 4A, the vertical member 450 may be a plate secured to the implant device by a securing element such as a screw mating with plate holes 452 or the through hole of the staple plate. FIG. 4B shows a plate as a vertical member 450 with different dimensions to support different alignment corrections in different or multiple planes. Consistent with the configuration of the embodiments of FIGS. 4D and 4E, the vertical member 450 has different dimensions to help alter the alignment of the spine in different planes. As shown, the lateral dimension anterior LDA on the anterior end 450A of the vertical member 450 as installed is longer than the lateral dimension posterior LDP on the posterior end 450P to reflect an implant system altering the alignment of the spine in the sagittal plane. As shown in FIG. 4C, the vertical member 450 may be a bracket secured to the staple plate by a screw mating with plate holes 452 or the through hole of the implant device. FIGS. 4D and 4E show an osteotomy 412 and a bracket as a vertical member 450 with different dimensions to support different alignment corrections in multiple planes. FIG. 4D illustrates an installed implant system from an anterior view with the vertical member 450 aligned at an oblique angle. FIG. 4E illustrates a lateral view of the vertical member 450 aligned at an oblique angle. In FIGS. 4D and 4E, the vertical member 450 has a longer leg defined by the anterior end 450A anterior to the spine when compared to the leg defined by the dimension of the posterior end 450P positioned in a position more posterior to the spine. This configuration of legs for the vertical member 450 reflects an implant system altering the alignment of the spine in the sagittal plane.

Figure 5A:
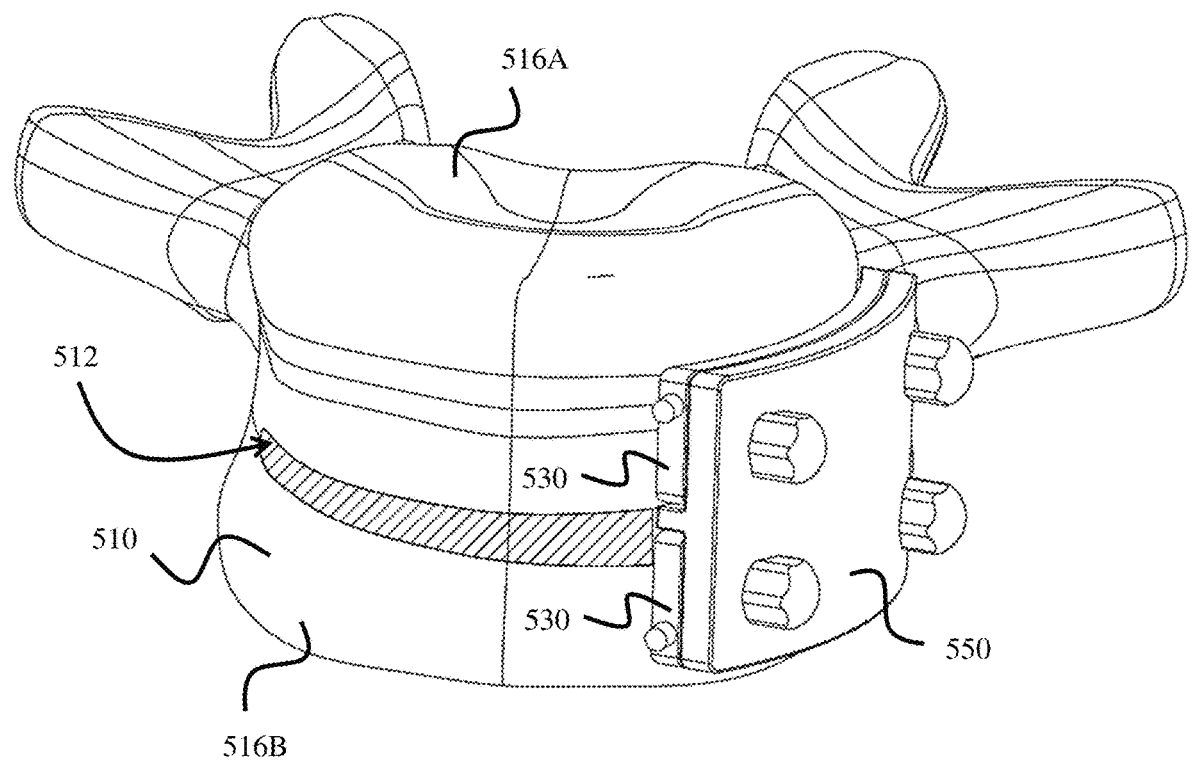
FIGS. 5A-5C illustrate an example embodiment of a vertebral implant system with predefined offsets with FIG. 5A showing an implanted implant device, FIG. 5B showing an exploded view of the vertebral implant system and FIG.
Figure 5B:
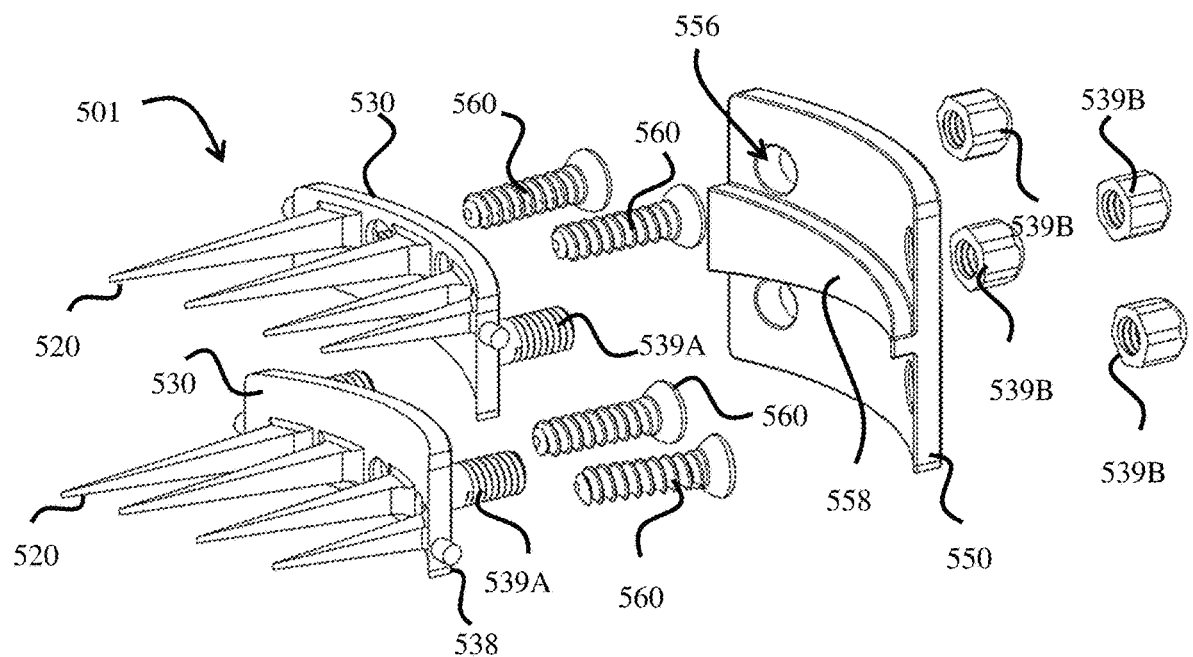
Figure 5C:
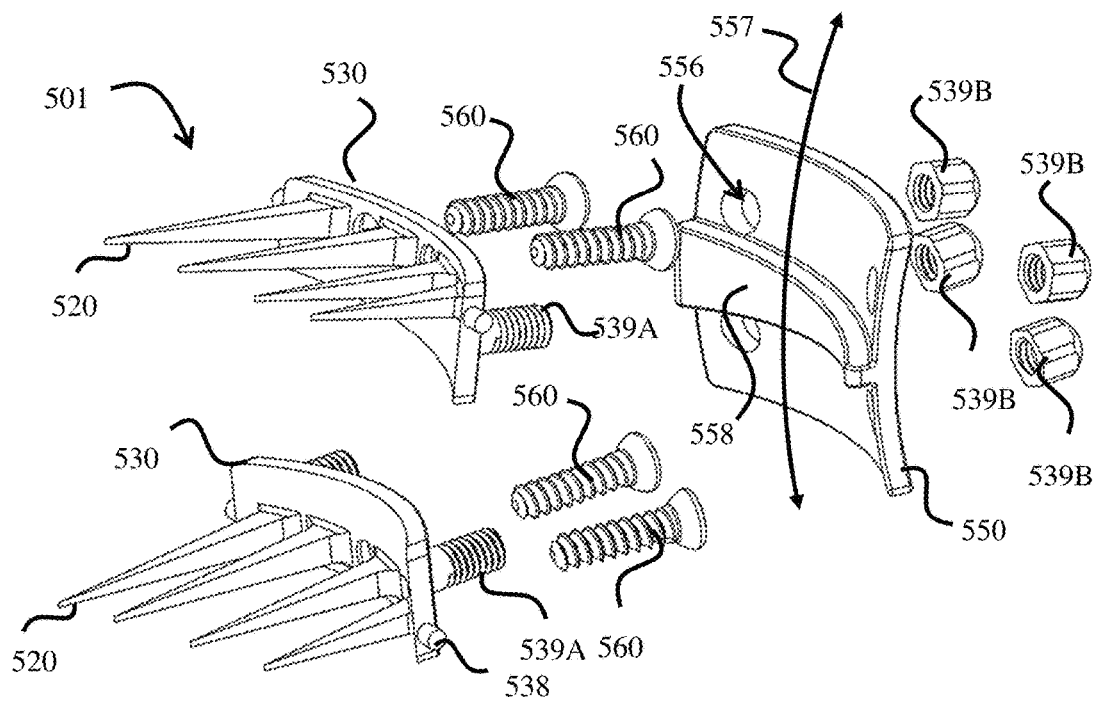

Another example embodiment a vertebral implant system is shown in FIGS. 5A-5C. Consistent with the embodiments described above, as shown in FIG. 5A, the staples (extending from staple plates 530) are configured to have the corresponding staple tines secured beneath the apophyseal rings and of the vertebral body 510. FIG. 5A illustrates an example embodiment of using multiple staples with one set of staple tines positioned under the superior end plate 516A and one set of staple tines positioned above the inferior end plate 516B. FIG. 5A illustrates an oblique view with the osteotomy 512 and staple tines positioned to alter the spine alignment in the coronal plane to correct deformities such as scoliosis. Consistent with embodiments described herein, the osteotomy 512 may be made from, and the staples with corresponding staple tines may be positioned from, oblique or anterior angles to alter the spine in the sagittal plane to correct deformities such as lordosis or kyphosis.

As shown in the embodiment of FIG. 5B, the vertebral implant system generally comprises a vertebral implant device comprising a staple 501 having one or more staple tines 520 extending from a staple plate 530 and a vertical member 550. As with the other embodiments, the configuration of the multiple staple tines 520 with spacing between them is to allow ample blood supply to still reach the entire vertebral endplates both superior and inferior of the vertebral bodies when the staple 501 is positioned in the vertebral body. In addition, the spacing allows ample blood supply to continue to provide nutrients to the intervertebral disc. The staple tines 520 generally extend from the staple plate 530 and the staple plate 530 generally couples the staple tines 520 together. The staple tines 520 are configured to cross the vertebral body in approximation to the end plate and apophyseal ring. In some embodiments, the staple tines 520 may be configured to be bi-cortical. The staple 501 may be anchored to the vertebral body by bone screws 560 received through recesses in the staple plate 530. The positioning of the staple tines 520 in the vertebral body, and the positioning of the upper tines relative to the lower staple tines define the offset dimension quantifying the alteration made to the end plate planes of the vertebral body. The offset dimension is the difference in the orientation of the end plates of the vertebral body and may be generally equivalent to the gap between the inner surfaces of the vertebral member that has been opened with a partial or through osteotomy.

FIGS. 5A-5C also show instrument alignment prongs 538 that may be positioned on different surfaces of the staple plate to allow the staple to be positioned and maneuvered with an external tool that removably couples to these alignment prongs.

Referring to FIGS. 5B and 5C, the vertebral implant system further comprises a vertical member 550. The vertical member 550 generally functions to stabilize the implant device and fix the gap formed by the osteotomy as the offset dimension. The vertical member 550 may be secured to the staple 501 through any suitable coupling method. In the embodiment shown, the vertical member 550 is coupled to the staple 501 through threaded posts 539A that are configured to extend from the staple plate 530 through holes 556 in the vertical member 550 and couple the staple plate 530 with a coupling element such as threaded nuts 539B. The vertical member 550 may be one of multiple different sized members to provide configurability to the implant system. The vertical members 550 may have different heights and configurations to correct different degrees of coronal plane wedging and they may also be different heights anterior versus posterior to adjust for sagittal plane vertebral body deformity. Consistent with the configuration of the embodiments of FIGS. 4A and 4E, the vertical member 550 elements may have different dimensions to help alter the alignment of the spine in different planes.

FIG. 5B shows a plate as a vertical member 550 with different dimensions to support different alignment corrections in different or multiple planes. As shown, the plate has an offset guide 558 protruding from a surface of the vertical member 550 to define an offset dimension between the upper and lower staples 520. The offset guide 558 is a protrusion from the inner surface of the vertical member 550 to fit within the osteotomy to help position the upper and lower staples 520 and to ensure a proper offset dimension of the vertebral end plate planes. In the configuration shown, the dimensions of the staples and the staple plate are consistent whereby the offset guide 558 generally defines an angle of the offset dimension. It is also understood that the angle of the offset dimension may be defined by dimensions of the staple plate and/or the positioning of the through holes in the plate. As shown in FIG. 5B, the offset guide 558 is configured to provide a sagittal adjustment when the vertebral implant system is implanted from a lateral approach.

FIG. 5C shows an alternative configuration of the plate. As shown, the plate has a curved shape to provide an offset curve 557 that allows for additional angles of the offset dimension. This curve may be convex or concave as desired. As shown, the offset curve 557 provides an offset dimension to provide a coronal adjustment when the vertebral implant system in implanted from a lateral approach. As show, the offset guide 558 may also provide a sagittal adjustment with the same vertical member.

Embodiments of the implant system may be configured to alter the alignment of the spine in multiple planes. This multi-plane alignment may be made by the insertion angle of the implant and/or the configuration of the staple tines and/or the dimensions of the vertical member.

The vertical member may be an individual member, a plate or multiple members. The vertical members may also connect two or more implant devices in a construct. The vertical member may also be integral to one or both of the staple plates.

The vertical members may be fixed or adjustable. Fixed and adjustable members can be used in combination.

In embodiments where the vertical member is an adjustable member, the adjustability may take advantage of an expanding force from the adjustable member to elongate or compress the bone based on Wolff's Law. The force may be applied by an elastic force within the adjustable member resulting from a tension or compression of components of the adjustable member. By configuring the expanding force to exceed a minimum effective strain value of the bone, similar to orthodontic applications, the application of the force on the bone results in a strain deformation of the bone. For example, putting a tension on the bone along its longitudinal axis by forcing two staples apart, the bone expands or lengthens along that axis.

Suitable ranges of force, as pressure, to be applied to the bone generally should be within the strength limits of cortical bone. Megapascal (MPa) is a unit in the category of Pressure, also known as megapascals where one pascal is defined as one newton per square meter. Megapascal (MPa) has a dimension of $ML^{-1}T^{-2}$ where M is mass, L is length, and T is time. It can be converted to the corresponding standard SI unit Pa by multiplying its value by a factor of 1000000. Although the values will be unique to each individual, typical upper limits of the strength of cortical bone along its longitudinal axis, in MPa, are shown in the table below:

TABLE 1

| Longitudinal [MPa] | | |
|---|---|---|
| | Compression | 193 |
| | Tension | 133 |
| | Modulus | 17,000 |
| | Poisson's Ratio | 0.40 |

From: Hart N H, Nimphius S, Rantalainen T, Ireland A, Siafarikas A, Newton R U. Mechanical basis of bone strength: influence of bone material, bone structure and muscle action. J Musculoskelet Neuronal Interact. 2017 Sep. 1; 17(3):114-139. PMID: 28860414; PMCID: PMC5601257.

Consistent with the above values, the desired tensile pressure applied to bone through an adjustable element will typically be less than 133 MPa and should be above the minimum effective strain value for the bone. Compressive forces should also be less than the compression limits of the bone.

Referring to the example embodiment in FIG. 6A, the vertical member may be an adjustable element 650 to allow for adjustment of the implant system during or post implantation. As shown in FIG. 6A, the vertical member may be one or more adjustable element 650 secured to the staple plate 630 by a screw mating with member through holes 652 and the hole of the staple plate 630. The adjustable element 650 may be any type of element that allows for the adjustment of either of its ends to alter the overall length of the adjustable element 650 while generally retaining its adjusted dimension once adjusted. For example, the adjustable element 650 may be a combination of rigid threaded elements that cooperate to alter the length of the element by turning one threaded element relative to the other.

One example embodiment of an adjustable element 650 as the vertical member is shown in FIG. 6B. As shown, the adjustable element 650 comprises a turnbuckle 635, threaded struts 633A and 633B, anchor eyes 631A and 631B and an engagement element 637. The turnbuckle 635 generally adjustably couples the struts 633A and 633B and provides a means to adjust the overall dimensions of the adjustable element 650. For example, the turnbuckle 635 may have a threaded recess to mate with external threads of the struts whereby when the turnbuckle 635 is rotated, the threads of the recess engage the threads of the struts 633A and 633B and the struts 633A and 633B are urged out of the threaded recess to make the overall length of the adjustable element 650 longer. Consistently, when the turnbuckle 635 is rotated in the opposite direction, the overall length of the adjustable element 650 is shorter. In some embodiments, an engagement element 637 is provided to allow the turnbuckle 635 to be moved so that it's dimensions can be altered. For example, as shown, the engagement element 637 comprises a turnbuckle wrench channel that can be engaged by an engagement tool such as a wrench to allow the wrench to rotate the turnbuckle 635. Other example embodiments of an engagement element 637 may be one or more recesses in the body of the turnbuckle 635 which can be engaged by the end of a rod, pin, or other engagement tool that can turn the turnbuckle 635. As shown, in embodiments where the struts 633A and 633B couple to the turnbuckle 635 with threads, the threads are configured such that the turning of the turnbuckle 635 lengthens the overall length of the adjustable element 650 when turned in one direction and shortens the overall length when turned in the other direction. As shown, the anchor eyes 631A and 631B define through holes 632A and 632B that may receive a coupling element, like a screw, to secure the adjustable element 650 to the staple plate. Also as shown, the threading of the upper and lower struts is in opposing directions. This is to allow the adjustable member to be expanded by turning the turnbuckle in one direction.

FIG. 6C illustrates details of another example embodiment of a vertical member 650. As shown, the adjustable element 650 comprises a keyed turnbuckle assembly divided into turnbuckles 635A and 635B, threaded struts 633A and 633B, anchor eyes 631A and 631B and an engagement element 637. As with the embodiment in FIG. 6B, the turnbuckles 635A and 635B generally adjustably couple the struts 633A and 633B and with the engagement element 637 provide a means to adjust the overall dimensions of the adjustable element 650. In this example, the engagement element 637 comprises a keyed edge on each of the turnbuckles whereby a mating key (not shown) can be inserted into the space between the keyed edges, the mating key engages both of the keyed edges, and when the mating key is rotated, the turnbuckles 635A and 635B are rotated (example direction shown) about the longitudinal axis of the vertical member and about the struts 633A and 633B. In this example, the turnbuckles 635A and 635B also have a threaded recess on the opposite ends to mate with external threads of the struts whereby when the turnbuckles 635A and 635B are rotated, the threads of the recess engage the threads of the struts 633A and 633B and the struts are urged out of the threaded recess to make the overall length of the adjustable element 650 longer. Consistently, when the mating key is rotated in the opposite direction, the overall length of the adjustable element 650 is shorter. Also as shown, the threading of the upper and lower struts is in the same direction to allow the adjustable member to be expanded by turning of the mating key.

The above embodiments of the adjustable member may be configured to apply the appropriate pressure by applying a force based on the modulus of elasticity and the shape of components of the adjustable member. The force may be provided by the elastic properties of the components, the shape of the component or a combination of the properties and the shape. Adjustable member components and their design may be selected that have elastic properties suitable to be deformed/compressed as the adjustable member is adjusted and then apply that elastic force (based on the shape and modulus of elasticity) to the staples and have that translated as an expanding force to the bone over time until the adjustable member achieves equilibrium. At equilibrium, the adjustment member may be activated again to apply further force on the bone.

The selection of the adjustable member properties may account for the weight of the body on the vertebrae to exceed the minimum effective strain on the bone. Also, the adjustable member may be designed to apply the force as the person is resting and not putting a vertical load on the bone.

In some embodiments, the vertebral implant system may be used to adjust a rotation of the end plate planes of the vertebral body. For example, the alignment of the spine may benefit from rotating one end plate plane relative to the other. To create this rotational alteration, the rotation of one end plate plane made be made manually and the implant device may be secured to the vertebral body while this alteration is manually maintained. Also, the rotational alteration may be made by having an adjustable element coupled to the staple plate in a manner that rotates one end plate plane relative to the other as the adjustment element is adjusted. For example, adjustable elements could be mounted to an upper and a lower staple in a horizontal or diagonal manner whereby when the adjustable element is adjusted, it urges a rotation of the one end plate relative to the other.

Instruments may also be provided to ensure specific degrees of rotation of the end plate planes.

In some embodiments, adjustments may be made after the original surgery to implant the device. These adjustments may be made with surgical procedures or non-surgical procedures and may employ the effect of Wolff's Law where the bone responds to force to attain a level of stress, similar to how adjustments of teeth are made in the field of orthodontia. These adjustments may be beneficial for particular applications such as but not limited to:
- spinal adjustments in the immature developing spine, as growth can be accommodated and correction adjusted;
- where additional foraminal indirect decompression is needed; and
- where additional deformity correction may be desired after the patient stands up.

These adjustments may be provided by mechanisms such as but not limited to:
- an externally activated component within the vertebral implant that is configured to be activated by an electromagnetic field, RFID, or other external field to cause the implant to produce a force on the fused vertebral body to change correction; and
- a percutaneous mechanism within the vertebral implant would be activated by a percutaneous puncture of a tool and a small diameter tool to engage with the implant and cause the implant to extend or collapse.

Another example embodiment of an adjustable element as the vertical member is shown in FIGS. 7A-7E. In this embodiment, referring to FIG. 7B, the adjustable element is a strain inducer 750 coupled to an upper staple 730A and lower staple 730B. Generally, the strain inducer 750 operates to provide adjustable strain forces on the vertebral body to influence the offset dimension between the two end plates of the vertebral body over time.

In one embodiment, the strain inducer is a thermal ratchet assembly that adjusts by receiving RF signals from a RF transmitter to heat and alter dimensions of the rachet elements to alter forces provided by the inducer on the vertebral body. As shown in FIGS. 7B, the strain inducer 750 comprises an upper body 735A configured to be coupled to the upper staple with through hole 732A and coupling element 752, a lower body 735B configured to be coupled to the lower staple with through hole 732B and coupling element 752, and a ratchet mechanism to adjust the two plates relative to each other. The ratchet mechanism includes one of the plates functioning as a linear rack plate with a toothed surface, the other plate functioning as a component of an adjustable mount. The adjustable mount couples the pawl element to other ratchet mechanism elements so that the pawl can adjustably engage the toothed surface of the rack plate and adjust the upper body 735A in relation to the lower body 735B. As shown in the exploded view of FIG. 7C, the upper body 735A with its teeth 744B function as the rack plate. The pawl 740 with its teeth 744A function as the ratchet pawl. The lower body 735A is one component of the adjustable mount and generally comprises an anchor for an adjustable member, here Nitinol wire 744, and an anchor for a tension member, here springs 742. The other elements of the adjustable mount generally comprises the (a) Nitinol wire 744 and the wire anchor 746 (as secured to the pawl 740 and the lower body 735B) and (b) the springs 742 (as secured to the pawl 740 and the lower body 735B (see FIG. 7D)). Together, the rack plate, the pawl and the adjustable mount function as a ratchet mechanism to allow but limit the adjustment of the two plates to a single direction and at increments of one tooth at a time. It is understood that although the embodiments use the example of the adjustable member being a Nitinol (Nickel titanium) wire that shortens and the tension member being springs that are extended to provide tension, other suitable materials that provide the appropriate properties may be used.

The adjustable mount provides the adjustability for the thermal ratchet assembly. Referring to FIGS. 7C-7E, the adjustable mount comprises the lower body 735B, one or more spring 742 coupled to the pawl 740 and the lower body 735B and one or more Nitinol wire 744 coupled to the pawl 740 and lower body 735B. In some embodiments, a mount slide is also provided to limit the movement of the pawl 740. As shown in FIGS. 7D and 7E, the mount slide may be defined by a channel that retains the upper body 735A. This channel may be defined by a back support 739 that retains the upper body 735A within a certain range of motion relative to the lower body 735B and the pawl 740 when retained in the lower body 735B.

The adjustable mount functions by allowing the pawl to move relative to and to engage the teeth on the rack plate. The adjustable mount also allows the pawl 740 to move based on forces applied to the pawl 740 from the springs 742 or the Nitinol wire 744. The forces from the Nitinol wire 744 are generally applied over a short term based on its shortening due to heat from the RF receiver. The forces from the spring 742 are generally applied over a longer time from the tensile properties of the spring 742.

The thermal ratchet assembly adjusts by receiving a frequency-specific electromagnetic field from an electromagnetic transmitter to excite the implanted receiver 737 and cause electrical energy to pass through the wire mount 738 as heat to the Nitinol wire 744 in the thermal ratchet. At temperature (selectable during alloy creation) the Nitinol wire 744, acting as an adjustable mount component, shortens by a dimension to reposition and reset the pawl teeth 748A against teeth 748B in the mating teeth of the rack. The dimension of the shortening of the Nitinol wire may be in the range of about 5%-10% of its length, it may be in a range of about 6%-9% of its length and in some embodiments the dimension may be about 7% of its length. The dimension of the teeth on the pawl and the rack are configured to coincide with the planned shortening of the wire so that the pawl moves at least one tooth relative to the rack with the wire shortens. When the temperature is removed, the Nitinol wires 744 will produce an expanding force against the pawl teeth 748A at the force of the material modulus of elasticity of the Nitinol. Additionally, the spring 742, acting as another adjustable mount component, will provide a tensile force on the pawl 740 according to its properties such as its modulus of elasticity. In some embodiments, the mount slide, acting as another mount component, functions to restrict movement of the pawl 740 by configuring the slot to only allow a key on the pawl to move within certain dimensions. By mounting the Nitinol wire 744 of the adjustable mount on to the mounting plate (wire mount 738 and the lower body 735B), coupling the mounting plate to one of the staples of the implant system and coupling the rack plate (upper body 735A) to the other staple, the forces on the pawl 740 produce forces to expand the offset dimension between the two staples and the two end plates of the vertebral body.

Although the embodiments shown in FIGS. 7A-7E show a spring as a coiled spring, it is understood that the spring may be any shaped element that through its shape and elastic properties is able to provide a tensile force on the pawl. Also, although the embodiments shown in FIGS. 7A-7E show a Nitinol wire with a simple connection between the wire mount and the pawl, it is understood that the Nitinol wire may be designed with a different configuration. For example, and not for limitation, the Nitinol wire may be longer with a pulley system to allow for a longer length of wire to provide a greater shortening dimension. Also, although the Nitinol wire is specified to provide the shortening features of the adjustable mount, it is understood that other materials with similar properties may be utilized. Also, although the embodiments shown create an extension of the vertebral body by urging the upper and lower bodies away from each other, the ratchet mechanism may be configured to create a compression of the vertebral body by urging the upper and lower bodies towards each other.

The heating of the Nitinol wire may be done through methods such as inductive coupling where radio waves of high frequency (e.g., above 70,000 hertz (cycles per second)) are transmitted with a transmitter coil and received with a RF receiver coil; similar to the way a wireless charging device recharges a suitable cell phone. Any method of heating from the RF receiver may be used. In one embodiment, Joule heating, also known as resistive, resistance, or Ohmic heating, may be used to heat the Nitinol wire where the current created in the RF receiver is communicated to the Nitinol wire and the resistance properties of the Nitinol convert the current to heat.

The frequency-specificity allows for adjustment of multiple strain inducers in the same patient by having each strain inducer at a different frequency (per patient). The power comes from the transmitter so there are no implanted power sources. Actuating only one strain inducer can cause angular change in the bone. Similarly, raising one side faster than another can cause angular change in the bone. A typical application would result in change in the sagittal plane. Actuating both strain inducers implanted from a lateral position may also provide coronal and height correction.

Operationally, transcutaneous implant adjustment may be accomplished by transmitting a frequency-specific electromagnetic field with a transmitter to excite an implanted receiver and cause electrical energy to pass through the Nitinol wire as heat. At temperature (selectable during alloy creation) the power wire shortens by a dimension, such as about 7%. The shortening of the Nitinol wire causes the pawl to move one or more tooth along the rack plate, set in a new tooth position which increases the tensile force from the spring. This creates a tensile force on the pawl and creates a force causing extension of the vertebral body. By exceeding the bone's strain with this tensile force, elongation will occur based on Wolff's Law. This is like orthodonture where applying a force and the remodeling will result in strain deformation. Once the strain inducer is activated the bone will remodel and increase in length. Activating the strain inducer again causes the cycle to repeat. Multiple activations cause extensive lengthening of the bone.

Consistent with the selection of component materials in the embodiments of FIGS. 6B and 6C, the selection of component materials for the thermal ratchet assembly are based on the properties desired to be put on the vertebral body.

In other embodiments of the vertebral implant system consistent with the embodiment illustrated in FIG. 3D, embodiments of the vertebral implant system may have elements such as bone screws function to provide the features of staple tines of a staple.

FIGS. 8A and 8B illustrating an example embodiments of a tipped bone screw with FIG. 8A showing the tipped bone screw and FIG. 8B showing a screw driver 880 engaged with a tipped bone screw to anchor the tipped bone screw in the vertebral body. Referring to FIG. 8A which shows a tipped bone screw 860 suitable for providing the features of staple tines for the vertebral implant system. The tip portion 862 of the bone screw is configured to have a surface 861 that can be frictionally engaged by the securing element. The tip portion 862 may be configured to have features that facilitate this frictional engagement with other screw plate alignment system components. For example, the tip portion 862 may have a frictional surface, roughened surface or a radially ribbed surface. The bone screw 860 may have an engagement portion 864 to mate with a tool, such as a screw driver, to turn and insert the bone screw 860 into the vertebral body. The engagement portion 864 of the tipped bone screw 860 may comprise teeth 863 to mate with teeth on the screw driver tool. The bone screw 860 may have a threaded portion 866 with threads 865 to allow the bone screw 860 to be driven into and secured to the vertebral body. The threaded portion 866 is similar to common bone screws configured to secure the screw to the bone. FIG. 8B shows an example embodiment of a screw driver 880 with a handle and a shaft tipped with an engagement portion to mate with the engagement portion of the tipped bone screw.

FIGS. 9A-9F illustrate an example embodiment of a screw driver. FIG. 9A shows the screw driver 980 engaged with a tipped bone screw in a vertebral body. FIG. 9B illustrates a cut away profile B-B of FIG. 9A showing an upper staple with tipped bone screw 960 functioning as a staple tine. As detailed in FIG. 9B, the bone screw is a tipped bone screw 960 with the tip portion of the tipped bone screw configured to engage a hollow tip of the bone screw driver 980. The tip portion 962 is configured to extend beyond the engagement portion 964 of the tipped bone screw 960 and be received in a hollow tip 983 of the bone screw driver 980. The tip portion 962 is also configured to secure the tipped bone screw 960 to a staple plate or directly to a vertical member 950 through a screw plate alignment system. FIG. 9B also shows the forward portion of the screw driver 980 also has a drive stop 984 that limits the driving of the tipped bone screw 960.

FIG. 9C shows the screw driver positioned to be engaged with a tipped bone screw. FIG. 9D shows details of the screw driver and the tipped bone screw 960 showing its threaded portion 966, the engagement portion 964, the tip portion 962 and the engagement portion 982 of the screw driver. As shown, the tip of the tipped bone screw driver 980 is configured to receive the tip portion of the tipped bone screw 960 and engage the engagement portion 964 so that the tipped bone screw 960 may be turned and driven into the bone. FIG. 9E shows another view of the screw driver 980 positioned to be engaged with a tipped bone screw 960 and FIG. 9F showing another view of details of the screw driver engagement portion 982 and the tipped bone screw 960.

In some embodiments, components may be provided and used with the vertebral implant system to provide a screw plate alignment system. In these embodiments, the screw plate alignment system comprises elements to frictionally engage and couple the tipped bone screw (as a staple tine) to the staple plate or vertical member. FIGS. 10A-10D illustrate an example embodiment of a screw driver, a lock driver and other components that can be used with the tipped bone screw to provide the screw plate alignment system.

FIG. 10A shows a lock driver 1070 engaged with a tipped bone screw in a vertebral body. FIG. 10B shows a cut-away portion A-A of FIG. 10A showing a screw plate alignment system comprising the tip portion 1062 of the bone screw 1060, the interior surface of the through hole through the plate 1050, a locking element 1072, and a securing element 1090. As shown, the tip of the lock driver 1070 is configured with the locking element 1072. Generally, the locking element 1072 functions to frictionally lock the securing element 1090 around the tip portion 1062 of the bone screw 1060 and hold the securing element 1090 and tip portion 1062 in the through hole of the plate 1050. Also shown is the securing element 1090 positioned within the locking element 1072 so that the securing element 1090 and the locking element 1072 can be positioned over and around the tip portion of the bone screw. The tip of the lock driver 1070 allows the locking element 1072 to be "screwed" or otherwise inserted into the plate 1050 through hole so that the exterior surface of the locking element 1072 engages the interior surface of the plate 1050 through hole. The lock driver 1070 may also be configured to have a "break away" ability to allow the locking element 1072 to break off of the lock driver 1070 and secure the locking element 1072 with the implant system. As shows, a thin portion 1076 of the lock driver at the end of a tapered portion 1075 can be configured to break when a pre-determined amount of torque is applied with the lock driver 1070. With the malleable securing element 1090 in the gap between the tip portion 1062 of the bone screw and the interior surface of the locking element 1072, slight deviations in the alignment of the tipped bone screw 1060 and the plate 1050 are accommodated while still anchoring the bone screw 1060 and securing it to the plate 1050.

FIG. 10C shows an exploded view of the lock driver 1070 positioned to be engaged with a securing element and FIG. 10D shows details of the lock driver 1070 and securing element 1090. Referring to FIG. 10D, the locking element 1072 may be a hollow cylindrical wedge-shaped portion of the lock driver 1070 to frictionally engage the interior surface of the plate through hole and engage the exterior surface of the securing element. In some embodiments, the outer surface of the locking element 1072 is configured to facility frictional engagement with the plate through hole. For example, the outer surface make be roughened or may be radially threaded with threads 1074. In some embodiments, the locking element 1072 may include a longitudinal slit 1077 along its length to allow the locking element 1072 to reduce its circumference and provide more compressive force on the securing element 1090. In some embodiments, the lock driver 1070 may also include a longitudinal slit 1073 along a portion of its length to allow the locking element 1072 to reduce its circumference.

Also shown in FIG. 10D, the securing element 1090 generally comprises a shaped malleable element configured to frictionally engage the outer surface of the tipped bone screw and the interior surface of the locking element bore 1071. The securing element 1090 may be a hollow cylindrical sphere-shaped element with a through bore 1094 configured to engage the interior surface of the locking element bore 1071 and engage the exterior surface of the tip portion of the tipped bone screw. In some embodiments, the securing element 1090 is a malleable element to deform and mold around the tip portion and deform and mold within the locking element bore 1071 of the locking element 1072. Similar to the locking element 1072, the securing element 1090 may include a lengthwise slit 1092 to allow the securing element 1090 to reduce its circumference and provide more compressive force on the surface of the tip portion of the bone screw.

In embodiments, the interior surface of the through holes of the plate may be a tapered to accommodate the mating, wedge-shaped, locking element. The interior surface of the through hole may be configured to facilitate frictional engagement with the locking element. For example, the interior surface may be roughened or have a radial thread similar to pipe thread.

One Embodiment of the Vertebral Implant System in Operation:

Operation of one embodiment of the vertebral implant system generally comprises the following sequence of steps:

Surgical access is provided to the vertebral body. In an anterior approach, this may be provided with an incision in the front of the belly. Typically, with this approach, a vascular surgeon or general surgeon may work with a spinal surgeon with the vascular surgeon clearing the path to the spine. In an oblique approach, access may be provided through an incision to the side of the belly that avoids the patient's abdominal muscles, peritoneal cavity and the blood vessels running to and from the legs. Similarly, with a lateral approach, access may be provided through an incision to the patient's side that also avoids the patient's abdominal muscles, peritoneal cavity and blood vessels. With the oblique or lateral approaches, access may be provided without the need for an additional vascular or general surgeon.

A particular oblique approach, called the anterior-to-psoas (ATP) approach, may be used to access the vertebral body and implant the device. With this ATP approach, an oblique incision is made and any abdominal muscles are bluntly dissected. The retroperitoneal space is exposed and bluntly dissected to expose the psoas muscle. The psoas muscle or psoas tendon is retracted posteriorly to expose the spine and vertebral body. Once the psoas muscle is identified, the blades for retraction are positioned to define the surgical corridor for creating the osteotomy and implanting the device.

An osteotomy is made through the vertebral body inferior to the pedicle (see FIG. 1C).

One staple and its staple tines are inserted into the vertebral body (a) just inferior to the superior endplate of the vertebral body or (b) just superior to the to the inferior endplate of the vertebral body (see FIG. 2). Generally, the staple tines are secured to the vertebral body in or proximal to the dense apophyseal ring.

Another staple and its staple tines are inserted into the vertebral body just between the cortical bone and the other endplate of the vertebral body (see FIG. 2).

If multiple staples are used, an appropriately sized vertical member is then secured to both staple plates to lock the upper and lower staple plates together (see FIGS. 4A-4E). The selection of the vertical member, and its features and dimensions, is determined by the desired offset dimension desired from the vertebral implant system.

With a through osteotomy, the vertebral implant system can be used to adjust height and angles. With a partial osteotomy the vertebral implant system can adjust the angles relying on the remaining cortical shell to act as a pivot or constraint on degrees of freedom.

With an adjustable element as the vertical member, adjustments of the implant system may occur during or post implantation. The adjustable element may be adjusted directly with a tool such as a wrench-type tool or a mating key to alter the dimension of the adjustable element, or the adjustable element may be adjustable through a remotely activated mechanism such as a wirelessly activated adjusting component that adjusts according to commands from a wirelessly connected device.

One Embodiment of the Screw Plate Alignment System in Operation:

Operation of one embodiment of the screw plate alignment system generally comprises the following sequence of steps:

Surgical access is provided to the vertebral body and an osteotomy is made through the vertebral body inferior to the pedicle as described above.

A staple plate is positioned on the vertebral body (a) just inferior to the superior endplate of the vertebral body or (b) just superior to the to the inferior endplate of the vertebral body.

A bone screw is positioned through the staple plate through hole and screwed into the vertebral body with the screw driver. The screw driver drives the bone screw into the bone until the drive stop limit of the screw driver hits the staple plate surface limiting the insertion of the screw to a predefined limit. The screw driver is removed and the process is repeated for other bone screws.

With the tipped bone screw positioned in the bone and the staple plate, the securing element is positioned in the hollow tip of the lock driver and the bore of the securing element is positioned over the tip of the bone screw with the lock driver. The tapered end of the locking element is then pushed into the threaded recess of the staple plate through hole and the lock driver is turned to have the exterior surface of the locking element engage the threads on the interior surface of the through hole. When the locking element is secure, a torque limit is reached at the tip of the lock driver and the locking element is broken off and left anchored to the staple plate. The lock driver, securing element and locking element are replaced and this step is repeated for another tipped bone screw until the staple plate and bone screws are secured to the vertebral body.

With one of the staple plates secured to one portion of the vertebral body, another staple plate and tipped bone screws are secured to the other portion of the vertebral body.

With the tipped bone screws and staple plates secured to the vertebral body, the vertical member is secured to the staple plate. This is typically achieved by screwing ends of the vertical member to the upper and lower staple plates. The selection of the vertical member, and its features and dimensions, is determined by the desired offset dimension desired from the vertebral implant system. And consistent with other embodiments, with an adjustable element as the vertical member, adjustments of the implant system may occur during or post implantation.

It is understood that the method may also be performed by securing each tipped bone screw to the staple plate before moving the next tipped bone screw.

Although this invention has been described in the above forms with a certain degree of particularity, it is understood that the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention which is defined in the claims and their equivalents.

We claim:

1. A vertebral implant system comprising:
   an upper staple;
   a lower staple;
   a vertical member configured to be coupled to the upper staple and the lower staple;
   the vertical member comprises a rachet assembly; and
   the rachet assembly comprising:
      a rack,
      a pawl configured to engage the rack,
      the pawl coupled to an adjustable mount,
      the adjustable mount comprising an adjustable member and a tension member,
      a radio frequency (RF) receiver configured to receive an RF signal from an electromagnetic transmitter,
      the adjustable member comprises a Nitinol wire, and
      the RF receiver configured to communicate the RF signal to an inducer whereby the inducer heats the Nitinol wire.

2. The vertebral implant system of claim 1 wherein the adjustable member is configured to be adjusted by one selected from the group consisting of:
   a percutaneous puncture and a small diameter tool; or
   an electromagnetic mechanism.

3. The vertebral implant system of claim 1 wherein the vertebral implant system is configured to correct both a coronal and a sagittal deformity of a vertebral body after an anterior vertebral body osteotomy.

4. The vertebral implant system of claim 1 wherein the vertical member is configured to correct both a coronal and a sagittal deformity of a vertebral body after an anterior vertebral body osteotomy performed through an anterior, lateral, or oblique approach to the vertebral body.

5. The vertebral implant system of claim 1 wherein the vertebral implant system comprises a vertebral implant device configured to be positioned as one of:
   an intervertebral implant device positioned between a first vertebral body and a second vertebral body; and
   an intravertebral implant device positioned between a first portion and a second portion of a single vertebral body.

6. The vertebral implant system of claim 1 wherein the heating of the Nitinol wire shortens a length of the Nitinol wire.

7. The vertebral implant system of claim 1 wherein the heating of the Nitinol wire shortens a length of the Nitinol wire and the tension member is configured to provide a force to urge the vertical member to have a greater length.

8. The vertebral implant system of claim 1 wherein the heating of the Nitinol wire shortens a length of the Nitinol wire and the tension member is configured to provide a force to urge the vertical member to have a shorter length.

9. A method of correcting a deformity of a vertebral body after a vertebral body osteotomy with a vertebral implant system, the method comprising:
   providing a vertebral implant system comprising:
      an upper staple;
      a lower staple;
      a vertical member configured to be coupled to the upper staple and the lower staple;
      the vertical member comprises a rachet assembly;
      the rachet assembly comprising:
         a rack,
         a pawl configured to engage the rack,
         the pawl coupled to an adjustable mount, and
         the adjustable mount comprising an adjustable member and a tension member,
         a radio frequency (RF) receiver configured to receive an RF signal from an electromagnetic transmitter,
         the adjustable member comprises a Nitinol wire, and
         the RF receiver configured to communicate the RF signal to an inducer whereby the inducer heats the Nitinol wire;
   inserting the upper staple into a first portion of the vertebral body;
   inserting the lower staple into a second portion of the vertebral body; and securing the vertical member to the upper staple and the lower staple whereby the vertebral implant system is secured to the vertebral body to correct the deformity of the vertebral body.

10. The method of claim 9 wherein the vertebral implant system is configured to correct both a coronal and a sagittal deformity of a vertebral body after an anterior vertebral body osteotomy.

11. The method of claim 9 wherein the vertical member is configured to correct both a coronal and a sagittal deformity of a vertebral body after an anterior vertebral body osteotomy performed through an anterior, lateral, or oblique approach to the vertebral body.

12. The method of claim 9 wherein the vertebral implant system comprises a vertebral implant device configured to be positioned as one of:

an intervertebral implant device positioned between a first vertebral body and a second vertebral body; and an intravertebral implant device positioned between a first portion and a second portion of a single vertebral body.

13. The method of claim 9 wherein the adjustable member is configured to be adjusted by one selected from the group consisting of:

a percutaneous puncture and a small diameter tool; or an electromagnetic mechanism.

14. The method of claim 9 wherein the heating of the Nitinol wire shortens a length of the Nitinol wire.

15. The method of claim 9 wherein the heating of the Nitinol wire shortens a length of the Nitinol wire and the tension member is configured to provide a force to urge the vertical member to have a greater length.

16. The method of claim 9 wherein the heating of the Nitinol wire shortens a length of the Nitinol wire and the tension member is configured to provide a force to urge the vertical member to have a shorter length.

\* \* \* \* \*